(12) United States Patent
Sugimoto et al.

(10) Patent No.: US 12,317,894 B2
(45) Date of Patent: Jun. 3, 2025

(54) COMPOSITION FOR STERILIZATION AND CLEANING, METHOD FOR PRODUCING SAME, AND STERILIZATION AND CLEANING METHOD EMPLOYING SAME

(71) Applicant: MITSUBISHI GAS CHEMICAL COMPANY, INC., Chiyoda-ku (JP)

(72) Inventors: Takashi Sugimoto, Katsushika-ku (JP); Syugo Sato, Katsushika-ku (JP); Susumu Innan, Katsushika-ku (JP); Ken-ichi Kimizuka, Chiyoda-ku (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 824 days.

(21) Appl. No.: 17/292,225

(22) PCT Filed: Nov. 11, 2019

(86) PCT No.: PCT/JP2019/044203
§ 371 (c)(1),
(2) Date: May 7, 2021

(87) PCT Pub. No.: WO2020/100837
PCT Pub. Date: May 22, 2020

(65) Prior Publication Data
US 2021/0400961 A1 Dec. 30, 2021

(30) Foreign Application Priority Data

Nov. 12, 2018 (JP) .................................. 2018-212261
Jun. 26, 2019 (JP) .................................. 2019-118563

(51) Int. Cl.
| | | |
|---|---|---|
| *A01N 37/36* | (2006.01) | |
| *A01N 25/02* | (2006.01) | |
| *A01N 25/22* | (2006.01) | |
| *A01N 25/30* | (2006.01) | |
| *A01N 37/02* | (2006.01) | |
| *A01N 57/00* | (2006.01) | |
| *A01N 59/00* | (2006.01) | |
| *C11D 1/06* | (2006.01) | |
| *C11D 3/04* | (2006.01) | |
| *C11D 3/20* | (2006.01) | |
| *C11D 3/33* | (2006.01) | |
| *C11D 3/36* | (2006.01) | |
| *C11D 3/48* | (2006.01) | |

(52) U.S. Cl.
CPC .............. *A01N 37/36* (2013.01); *A01N 25/02* (2013.01); *A01N 25/22* (2013.01); *A01N 25/30* (2013.01); *A01N 37/02* (2013.01); *A01N 57/00* (2013.01); *A01N 59/00* (2013.01); *C11D 1/06* (2013.01); *C11D 3/04* (2013.01); *C11D 3/20* (2013.01); *C11D 3/33* (2013.01); *C11D 3/36* (2013.01); *C11D 3/48* (2013.01)

(58) Field of Classification Search
CPC ........ A01N 25/22; A01N 25/30; A01N 37/02; A01N 57/00; A01N 59/00; C11D 1/06; C11D 3/04; C11D 3/48; C11D 11/0094; C11D 3/0084; C11D 3/361; B08B 3/08
See application file for complete search history.

(56) References Cited

U.S. PATENT DOCUMENTS

| | | | | |
|---|---|---|---|---|
| 3,114,606 A | * | 12/1963 | Meeker | .................. C01B 15/037 |
| | | | | 423/273 |
| 2004/0127381 A1 | | 7/2004 | Scialla et al. | |
| 2010/0048730 A1 | | 2/2010 | Li et al. | |
| 2010/0076082 A1 | | 3/2010 | Gamet et al. | |
| 2011/0293741 A1 | | 12/2011 | Kawamukai et al. | |
| 2015/0314025 A1 | | 11/2015 | Berentsveig et al. | |
| 2016/0121010 A1 | * | 5/2016 | Harada | ................... A61L 2/186 |
| | | | | 422/28 |
| 2016/0330970 A1 | | 11/2016 | Qian | |

FOREIGN PATENT DOCUMENTS

| | | | | |
|---|---|---|---|---|
| EP | 1 123 655 A1 | | 8/2001 | |
| GB | 2 301 111 A | | 11/1996 | |
| JP | 63-286158 A | | 11/1988 | |
| JP | 1-97920 A | | 4/1989 | |
| JP | 6-340317 A | | 12/1994 | |
| JP | 8-311495 A | | 11/1996 | |
| JP | 2003-48877 A | | 2/2003 | |
| JP | 2004-109087 A | | 4/2004 | |
| JP | 2006-193631 A | | 7/2006 | |
| JP | 2007-507599 A | | 3/2007 | |
| JP | 2008-138027 A | | 6/2008 | |
| JP | 2010/095448 | * | 4/2010 | ............. A01N 37/02 |
| JP | 2010-95448 A | | 4/2010 | |
| JP | 2010095448 A | * | 4/2010 | |
| JP | 2010-523784 A | | 7/2010 | |

(Continued)

OTHER PUBLICATIONS

JP-2010095448-A Translated (Year: 2010).*
JP 2010/095448 Translated (Year: 2010).*
Yang, X.-Q., et al., "Study on the Industry—Applied Properties of Alkylethercarboxylates", China Surfactant Detergent & Cosemetics, 2001, first period, vol. 31, pp. 5-8 (with English abstract).
International Search Report issued on Dec. 10, 2019 in PCT/JP2019/044203 filed on Nov. 11, 2019, 3 pages.
International Search Report issued on Aug. 11, 2020 in PCT/JP2020/018593 filed on May 8, 2020, 3 pages.

(Continued)

*Primary Examiner* — Robert A Wax
*Assistant Examiner* — John Seungjai Kwon
(74) *Attorney, Agent, or Firm* — Oblon, McClelland, Maier & Neustadt, L.L.P.

(57) ABSTRACT

A composition for sterilization and cleaning which comprises 0.001-30 mass % peracetic acid, 0.001-30 mass % hydrogen peroxide, 1-70 mass % acetic acid and/or salt thereof, 0.001-5 mass % polyoxyethylene lauryl ether acetate or salt thereof, and water, the composition having a pH of 4.0-10.0.

18 Claims, No Drawings

(56) References Cited

FOREIGN PATENT DOCUMENTS

| | | |
|---|---|---|
| JP | 2010-184868 A | 8/2010 |
| JP | 2011-219610 A | 11/2011 |
| JP | 2013-505929 A | 2/2013 |
| JP | 2015-40209 A | 3/2015 |
| JP | 2016-17056 A | 2/2016 |
| JP | 2016-505564 A | 2/2016 |
| JP | 2016-532634 A | 10/2016 |
| WO | WO00/22931 A1 | 4/2000 |
| WO | WO 2010/095231 A1 | 8/2010 |
| WO | WO 2011/036628 A2 | 3/2011 |
| WO | WO 2014/089632 A1 | 6/2014 |
| WO | WO 2020/100837 A1 | 5/2020 |

OTHER PUBLICATIONS

Japanese Office Action mailed on Sep. 17, 2024, issued in Japanese Patent Application No. 2021-527438, with machine-generated English translation, total 13 pages.

* cited by examiner

COMPOSITION FOR STERILIZATION AND CLEANING, METHOD FOR PRODUCING SAME, AND STERILIZATION AND CLEANING METHOD EMPLOYING SAME

TECHNICAL FIELD

The present invention relates to a composition for sterilization and cleaning, which is particularly suitable for sterilization and/or cleaning a medical device.

BACKGROUND ART

Conventionally, a peracid aqueous solution has been widely used in the sterilization and/or cleaning of medical devices (Patent Literatures 1 to 4).

However, such a conventional peracid aqueous solution has not been necessarily satisfactory in terms of stability, sterilizing ability, and scale removal ability.

In addition, conventionally, acidic or alkaline drugs have been used in sterilization and/or cleaning of medical devices, and a peracid aqueous solution is also one of such acidic or alkaline drugs. However, due to the use of such acidic or alkaline drugs, the waste liquids thereof are often drained while they do not satisfy sewage discharge standards, and as a result, the waste liquids frequently give damage to sewer pipes made of concrete. The damage of sewer pipes hinders drainage to sewers and is also likely to cause road collapse. Thus, an immediate action needs to be taken to such damage of sewer pipes. Under such circumstances, Tokyo Metropolitan Government Bureau of Sewerage called attention to dialysis drainage and sewer pipes in January, 2019. Tokyo Metropolitan Government Bureau of Sewerage requires that, with regard to sewage discharge standards regarding drainage, the hydrogen ion concentration (pH) be set within the range of higher than pH 5 and lower than pH 9.

As peracetic acid compositions for sterilization and cleaning used in the sterilization and cleaning of medical devices, an acidic peracetic acid aqueous solution (Patent Literature 5), a composition containing an aluminum corrosion-inhibitory acidic oxidizer (Patent Literature 6), an alkaline formulation for sterilization and cleaning (Patent Literature 7), and the like have been known. However, it cannot be said that these compositions always satisfy the sewage discharge standards regarding drainage. Accordingly, there has still been a need for a cleaning agent that does not give damage to water pipes.

CITATION LIST

Patent Literature

Patent Literature 1: JP 2007-507599 A
Patent Literature 2: JP 2013-505929 A
Patent Literature 3: JP 2015-40209 A
Patent Literature 4: JP 2016-17056 A
Patent Literature 5: JP 2010-184868 A
Patent Literature 6: WO2010/095231
Patent Literature 7: JP 2016-532634 A

SUMMARY OF INVENTION

Technical Problem

A composition for sterilization and cleaning, the stability and sterilizing ability of which are improved and which further has scale removal ability, has been desired. Also, there has been a need for a composition for sterilization and cleaning of medical devices, which has high stability of peroxide and a drainage of which satisfies the sewage discharge standards.

Solution to Problem

As a result of intensive studies, the present inventors have found that, by adding a special anionic surfactant (polyoxyethylene lauryl ether acetic acid) to peracetic acid, a composition for sterilization and cleaning, having improved stability and sterilizing ability compared with a conventional peracetic acid aqueous solution, and further having scale removal ability, can be provided. Moreover, the present inventors have also found that, by adding a phosphorus-based stabilizer and/or a carboxylic acid-based stabilizer as an additive(s), a composition for sterilization and cleaning of medical devices, which has high stability of peroxide and a drainage of which satisfies the sewage discharge standards, can be provided.

Specifically, the present invention includes the following embodiments.

<1>
A composition for sterilization and cleaning, which comprises 0.001% to 30% by mass of peracetic acid, 0.001% to 30% by mass of hydrogen peroxide, 1% to 70% by mass of acetic acid and/or a salt thereof, 0.001% to 5% by mass of polyoxyethylene lauryl ether acetic acid or a salt thereof, and water, wherein
the pH value of the composition for sterilization and cleaning is pH 4.0 to 10.0.
<2>
The composition according to the above <1>, further comprising a phosphorus-based stabilizer and/or a carboxylic acid-based stabilizer as an additive(s).
<3>
The composition according to the above <2>, comprising the phosphorus-based stabilizer and/or the carboxylic acid-based stabilizer in a concentration of 0.0001% to 5% by mass.
<4>
The composition according to the above <2> or <3>, wherein the phosphorus-based stabilizer is selected from the group consisting of pyrophosphoric acid or a salt thereof, phosphoric acid or a salt thereof, 1-hydroxyethylidene-1,1-diphosphonic acid (HEDP) or a salt thereof, diethylenetriamine penta(methylene phosphonic acid) (DTPP) or a salt thereof, nitrilotris(methylenephosphonic acid) or a salt thereof, 2-phosphonobutane-1,2,4-tricarboxylic acid or a salt thereof, and ethylenediamine tetra(methylene phosphonic acid) or a salt thereof, and the phosphorus-based stabilizer is preferably 1-hydroxyethylidene-1,1-diphosphonic acid (HEDP) or a salt thereof.
<5>
The composition according to the above <2> or <3>, wherein the carboxylic acid-based stabilizer includes any of ethylenediaminetetraacetic acid (EDTA) or a salt thereof, diethylenetriamine pentaacetic acid (DTPA) or a salt thereof, picolinic acid or a salt thereof, dipicolinic acid or a salt thereof, nitrilotriacetic acid or a salt thereof, N-(2-hydroxyethyl)ethylenediamine-N,N',N''-triacetic acid or a salt thereof, triethylenetetramine-N,N,N',N'',N''',N'''-hexaacetic acid or a salt thereof, 1,3-propanediamine-N,N,N',N'-tetraacetic acid, 1,3-diamino-2-propanol-N,N,N',N'-tetraacetic acid, N-(2-hydroxyethyl)iminodiacetic acid or a salt thereof, N,N-di(2-hydroxyethyl)glycine or a salt thereof, glycol ether diamine tetraacetic acid, and (S,S)-ethylenediamine-N,N'-disuccinic acid or a salt thereof, and the carboxylic acid-based stabilizer is preferably ethylenediaminetetraacetic acid (EDTA) or a salt thereof.

<6>

A diluted composition for sterilization and cleaning, which comprises:
  the composition according to any one of the above <1> to <5>; and
  additional water.

<7>

The diluted composition according to the above <6>, which comprises 0.001% to 1.5% by mass of peracetic acid, 0.001% to 2.5% by mass of hydrogen peroxide, 0.01% to 7% by mass of acetic acid and/or a salt thereof, and 0.00001% to 0.1% by mass of polyoxyethylene lauryl ether acetic acid or a salt thereof, wherein
  the pH value of the diluted composition is pH 4.0 to 10.0.

<8>

A method for producing the composition according to any one of the above <1> to <5>, comprising a mixing step of mixing at least the following components:
  (i) a hydrogen peroxide solution;
  (ii) acetic acid; and
  (iii) polyoxyethylene lauryl ether acetic acid or a salt thereof.

<9>

A method for producing the composition according to any one of the above <1> to <5>, comprising a mixing step of mixing at least the following components:
  (i) a phosphorus-based stabilizer and/or a carboxylic acid-based stabilizer used as an additive(s);
  (ii) a hydrogen peroxide solution and acetic acid;
  (iii) acetate; and
  (iv) polyoxyethylene lauryl ether acetic acid or a salt thereof.

<10>

A method for producing the composition according to any one of the above <1> to <5>, comprising a mixing step of mixing at least the following components:
  (i) a phosphorus-based stabilizer and/or a carboxylic acid-based stabilizer used as an additive(s);
  (ii) a hydrogen peroxide solution and acetic acid;
  (iii) alkali; and
  (iv) polyoxyethylene lauryl ether acetic acid or a salt thereof.

<11>

The method for producing the composition according to the above <10>, wherein the additive(s), acetic acid, alkali, and polyoxyethylene lauryl ether acetic acid or a salt thereof are mixed, and then the hydrogen peroxide solution is further mixed into the mixture at 30° C. to 50° C.

<12>

A method for producing the diluted composition according to the above <6> or <7>, comprising:
  a mixing step of mixing at least the following components; and
  a dilution step of diluting the obtained mixed solution:
  (i) a hydrogen peroxide solution and acetic acid;
  (ii) acetate or alkali; and
  (iii) polyoxyethylene lauryl ether acetic acid or a salt thereof.

<13>

The method for producing the diluted composition according to the above <12>, wherein the dilution step comprises mixing the mixture obtained in the mixing step with water.

<14>

A method for sterilizing and cleaning a medical device, using the composition according to any one of the above <1> to <5> or the diluted composition according to the above <6> or <7>.

<15>

The method for sterilizing and cleaning a medical device according to the above <14>, which is any one of an immersion method, a spray method, and a coating method.

<16>

The method for sterilizing and cleaning according to the above <14> or <15>, wherein the medical device is a dialyzer.

<17>

A composition for sterilization and cleaning, which comprises 0.01% to 30% by mass of peracetic acid, 0.1% to 30% by mass of hydrogen peroxide, 1% to 60% by mass of acetic acid, 0.001% to 5% by mass of polyoxyethylene lauryl ether acetic acid or a salt thereof, and water.

<18>

The composition according to the above <17>, further comprising a stabilizer.

<19>

The composition according to the above <18>, comprising the stabilizer in a concentration of 0.01% to 5% by mass.

<20>

The composition according to the above <18> or <19>, wherein the stabilizer is a phosphorus-based stabilizer.

<21>

The composition according to the above <20>, wherein the phosphorus-based stabilizer is selected from the group consisting of pyrophosphoric acid, phosphoric acid, 1-hydroxyethylidene-1,1-diphosphonic acid, nitrilotris(methylenephosphonic acid), 2-phosphonobutane-1,2,4-tricarboxylic acid, and ethylenediamine tetra(methylene phosphonic acid), and the phosphorus-based stabilizer is preferably pyrophosphoric acid.

<22>

The composition according to any one of the above <17> to <21>, further comprising a chelating agent.

<23>

The composition according to the above <22>, comprising the chelating agent in a concentration of 0.01% to 2% by mass.

<24>

The composition according to the above <22> or <23>, wherein the chelating agent is selected from the group consisting of ethylenediaminetetraacetic acid, citric acid, malic acid, 1-hydroxyethylidene-1,1-diphosphonic acid (HEDP), and dipicolinic acid.

<25>

A diluted composition for sterilization and cleaning, which comprises:
  the composition according to any one of the above <17> to <24>; and
  additional water.

<26>

The diluted composition according to the above <25>, which comprises 0.001% to 0.2% by mass of peracetic acid, 0.01% to 2% by mass of hydrogen peroxide, 0.01% to 1% by mass of acetic acid, and 0.00001% to 0.1% by mass of polyoxyethylene lauryl ether acetic acid or a salt thereof.

<27>

A method for producing the composition according to any one of the above <17> to <24>, comprising a mixing step of mixing at least the following components:

(i) a hydrogen peroxide solution;
(ii) acetic acid; and
(iii) polyoxyethylene lauryl ether acetic acid or a salt thereof.

<28>

A method for producing the composition according to any one of the above <17> to <24>, comprising the following steps (A) and (B):
  a step (A) of mixing, at least, acetic acid, 30% to 65% by mass of a hydrogen peroxide aqueous solution, and polyoxyethylene lauryl ether acetic acid or a salt thereof, and
  a step (B) of leaving an aqueous solution (a) obtained in the step (A) at rest at 20° C. to 60° C. for 1 day or more.

<29>

The method for producing the composition according to the above <28>, wherein the step (A) further comprises mixing a chelating agent.

<30>

A method for producing the composition according to any one of the above <17> to <24>, comprising the following steps (C) to (E):
  a step (C) of mixing, at least, acetic acid and 30% to 65% by mass of a hydrogen peroxide aqueous solution;
  a step (D) of leaving an aqueous solution (c) obtained in the step (C) at rest at 20° C. to 60° C. for 1 day or more; and
  a step (E) of mixing an aqueous solution (d) obtained in the step (D), polyoxyethylene lauryl ether acetic acid or a salt thereof, and water.

<31>

The method for producing the composition according to the above <30>, wherein, in the step (E), a chelating agent is further mixed.

<32>

A method for producing the diluted composition according to the above <25> or <26>, comprising:
  a mixing step of mixing at least the following components, and
  a dilution step of diluting the obtained mixed solution:
  (i) a hydrogen peroxide solution;
  (ii) acetic acid; and
  (iii) polyoxyethylene lauryl ether acetic acid or a salt thereof.

<33>

The method for producing the diluted composition according to the above <32>, wherein the dilution step comprises mixing a mixture obtained in the mixing step with water.

<34>

A method for sterilizing and cleaning a medical device, using the composition according to any one of the above <17> to <24> or the diluted composition according to the above <25> or <26>.

<35>

The method for sterilizing and cleaning a medical device according to the above <34>, which is any of an immersion method, a spray method, and a coating method.

<36>

The method for sterilizing and cleaning according to the above <34> or <35>, wherein the medical device is a dialyzer.

<37>

A composition for sterilization and cleaning, which comprises 0.001% to 15% by mass of peracetic acid, 0.01% to 70% by mass of acetic acid and/or a salt thereof, 0.001% to 25% by mass of hydrogen peroxide, and water, and also comprises, as an additive(s), a phosphorus-based stabilizer and/or a carboxylic acid-based stabilizer, wherein
  the pH value of the composition for sterilization and cleaning is pH 4.0 to 10.0.

<38>

The composition according to the above <37>, wherein the phosphorus-based stabilizer includes any of 1-hydroxyethylidene-1,1-diphosphonic acid (HEDP) or a salt thereof, and diethylenetriamine penta(methylene phosphonic acid) (DTPP) or a salt thereof, and the phosphorus-based stabilizer is preferably 1-hydroxyethylidene-1,1-diphosphonic acid (HEDP) or a salt thereof.

<39>

The composition according to the above <37> or <38>, wherein the carboxylic acid-based stabilizer includes any of ethylenediaminetetraacetic acid (EDTA) or a salt thereof, and diethylenetriamine pentaacetic acid (DTPA) or a salt thereof, and the carboxylic acid-based stabilizer is preferably ethylenediaminetetraacetic acid (EDTA) or a salt thereof.

<40>

The composition according to any one of the above <37> to <39>, wherein the phosphorus-based stabilizer is 1-hydroxyethylidene-1,1-diphosphonic acid (HEDP) or a salt thereof, and the carboxylic acid-based stabilizer is ethylenediaminetetraacetic acid (EDTA) or a salt thereof.

<41>

The composition according to any one of the above <37> to <40>, which comprises the phosphorus-based stabilizer in a concentration of 0.0001% by mass or more and less than 0.5% by mass, and the carboxylic acid-based stabilizer in a concentration of 0.0001% by mass or more and less than 0.5% by mass.

<42>

The composition according to any one of the above <37> to <41>, which further comprises one or more selected from a phosphate, a citrate, and a tris base.

<43>

The composition according to any one of the above <37> to <42>, which further comprises sodium stannate as an additive.

<44>

The composition according to the above <43>, comprising the sodium stannate in a concentration of 0.0001% to 5% by mass.

<45>

A composition for sterilization and cleaning, which comprises 0.001% to 15% by mass of peracetic acid, 0.01% to 70% by mass of acetic acid and/or a salt thereof, 0.001% to 25% by mass of hydrogen peroxide, and water, and also comprises sodium stannate as an additive, wherein the pH value of the composition for sterilization and cleaning is pH 4.0 to 10.0.

<46>

The composition according to the above <45>, comprising the sodium stannate in a concentration of 0.0001% to 5% by mass.

<47>

The composition according to the above <45> or <46>, further comprising a phosphorus-based stabilizer and/or a carboxylic acid-based stabilizer as an additive(s).

<48>

The composition according to the above <47>, which comprises the phosphorus-based stabilizer in a concentration of 0.0001% by mass or more and less than 0.5% by mass, and the carboxylic acid-based stabilizer in a concentration of 0.0001% by mass or more and less than 0.5% by mass.

<49>
The composition according to any one of the above <37> to <48>, the pH value of which is pH 5.0 to 9.0.

<50>
A diluted composition for sterilization and cleaning, which comprises:
the composition according to any one of the above <37> to <49>; and
additional water.

<51>
The diluted composition for sterilization and cleaning according to the above <50>, which comprises 0.001% to 1.5% by mass of peracetic acid, 0.01% to 7% by mass of acetic acid and/or a salt thereof, 0.001% to 2.5% by mass of hydrogen peroxide, and water, and also comprises a phosphorus-based stabilizer and/or a carboxylic acid-based stabilizer as an additive(s), wherein
the pH value of the diluted composition for sterilization and cleaning is pH 4.0 to 10.0.

<52>
The diluted composition for sterilization and cleaning according to the above <50>, which comprises 0.001% to 1.5% by mass of peracetic acid, 0.01% to 7% by mass of acetic acid and/or a salt thereof, 0.001% to 2.5% by mass of hydrogen peroxide, and water, and also comprises sodium stannate as an additive, wherein
the pH value of the diluted composition for sterilization and cleaning is pH 4.0 to 10.0.

<53>
The composition according to any one of the above <37> to <49> or the diluted composition according to any one of the above <50> to <52>, wherein the hydrogen peroxide is ultrapure hydrogen peroxide.

<54>
The composition according to any one of the above <37> to <49> or the diluted composition according to any one of the above <50> to <53>, wherein the acetic acid is ultrapure acetic acid.

<55>
A method for producing the composition according to any one of the above <37> to <49>, <53>, and <54>, comprising a mixing step of mixing at least the following components:
(i) an additive;
(ii) a hydrogen peroxide solution and acetic acid; and
(iii) one or more selected from a phosphate, a citrate, and a tris base.

<56>
A method for producing the composition according to any one of the above <37> to <49>, <53>, and <54>, comprising a mixing step of mixing at least the following components:
(i) an additive;
(ii) a hydrogen peroxide solution and acetic acid; and
(iii) alkali.

<57>
The method for producing the composition according to the above <56>, wherein the additive, acetic acid, and alkali are mixed, and then a hydrogen peroxide solution is further mixed into the mixture at 30° C. to 50° C.

<58>
A method for producing the composition according to any one of the above <37> to <49>, <53>, and <54>, comprising a mixing step of mixing at least the following components:
(i) an additive;
(ii) a hydrogen peroxide solution and acetic acid; and
(iii) acetate.

<59>
The method for producing the composition according to any one of the above <55> to <58>, wherein the mixing step further comprises adding a metal selected from the group consisting of Al, Zr, and Nb.

<60>
A method for sterilizing and cleaning a medical device, in which the composition according to any one of the above <37> to <49>, <53>, and <54>, or the diluted composition according to any one of the above <50> to <54> is used.

<61>
The method for sterilizing and cleaning a medical device according to the above <60>, which is any of an immersion method, a spray method, and a coating method.

<62>
The method for sterilizing and cleaning according to the above <60> or <61>, wherein the medical device is a dialyzer.

Advantageous Effects of Invention

According to one embodiment of the present invention, by adding a special anionic surfactant (polyoxyethylene lauryl ether acetic acid) to peracetic acid, a composition for sterilization and cleaning, having improved stability and sterilizing ability compared with a conventional peracetic acid aqueous solution, and further having scale removal ability, can be provided. According to another embodiment of the present invention, by adding a phosphorus-based stabilizer and/or a carboxylic acid-based stabilizer as an additive(s), a composition for sterilization and cleaning of medical devices, which has high stability of peroxide and a drainage of which satisfies the sewage discharge standards, can be provided. Since the pH value of the composition of the present invention satisfies the sewage discharge standards, a waste liquid after use can be drained without needing to be subjected to a neutralization treatment. All of the compositions of the present invention are suitable for sterilization and/or cleaning of medical devices, and in particular, dialyzers.

DESCRIPTION OF EMBODIMENTS

Embodiment A

A-1. Composition for Sterilization and Cleaning

The composition for sterilization and cleaning of the present invention comprises peracetic acid, hydrogen peroxide, acetic acid and/or a salt thereof, polyoxyethylene lauryl ether acetic acid or a salt thereof, and water.

In one embodiment of the present invention, the pH value of the composition for sterilization and cleaning may be pH 4.0 to 10.0. In one embodiment of the present invention, the pH value of the composition for sterilization and cleaning may be, for example, pH 4.0, 4.5, 5.0, 5.1, 5.2, 5.3, 5.4, 5.5, 5.6, 5.7, 5.8, 5.9, 6.0, 6.5, 7.0, 7.5, 8.0, 8.5, 9.0, 9.5, 10.0 or the like, but it is not limited to these values. In one embodiment of the present invention, the pH value of the composition for sterilization and cleaning may be, for example, pH 4.0 to 10.0, 4.0 to 9.5, 4.0 to 9.0, 4.0 to 8.5, 4.0 to 8.0, 4.0 to 7.5, 4.0 to 7.0, 4.0 to 6.5, or 4.0 to 6.0. In one embodiment of the present invention, the pH value of the composition for sterilization and cleaning may be pH 4.5 to 10.0, 4.5 to 9.5, 4.5 to 9.0, 4.5 to 8.5, 4.5 to 8.0, 4.5 to 7.5, 4.5 to 7.0, 4.5 to 6.5, or 4.5 to 6.0. In one embodiment of the present invention, the pH value of the composition for sterilization and cleaning may be pH 5.0 to 10.0, 5.0 to 9.5, 5.0 to 9.0, 5.0 to 8.5, 5.0 to 8.0, 5.0 to 7.5, 5.0 to 7.0, 5.0 to 6.5, or 5.0 to 6.0. In one embodiment of the present invention, the pH value of the composition for sterilization and cleaning may be pH 5.1 to 10.0, 5.1 to 9.5, 5.1 to 9.0, 5.1 to 8.5, 5.1 to 8.0, 5.1 to 7.5, 5.1 to 7.0, 5.1 to 6.5, or 5.1 to 6.0. In one embodiment of the present invention, the pH value of the composition for sterilization and cleaning may be pH 5.2 to 10.0, 5.2 to 9.5, 5.2 to 9.0, 5.2 to 8.5, 5.2 to 8.0, 5.2 to 7.5, 5.2 to 7.0, 5.2 to 6.5, or 5.2 to 6.0. In one embodiment of the present invention, the pH value of the composition for sterilization and cleaning may be pH 5.3 to 10.0, 5.3 to 9.5, 5.3 to 9.0, 5.3 to 8.5, 5.3 to 8.0, 5.3 to 7.5, 5.3 to 7.0, 5.3 to 6.5, or 5.3 to 6.0. In one embodiment of the present invention, the pH value of the composition for sterilization and cleaning may be pH 5.4 to 10.0, 5.4 to 9.5, 5.4 to 9.0, 5.4 to 8.5, 5.4 to 8.0, 5.4 to 7.5, 5.4 to 7.0, 5.4 to 6.5, or 5.4 to 6.0. In one embodiment of the present invention, the pH value of the composition for sterilization and cleaning may be pH 5.5 to 10.0, 5.5 to 9.5, 5.5 to 9.0, 5.5 to 8.5, 5.5 to 8.0, 5.5 to 7.5, 5.5 to 7.0, 5.5 to 6.5, or 5.5 to 6.0. Ina preferred embodiment of the present invention, the pH value of the composition for sterilization and cleaning is higher than pH 5.0. In a preferred embodiment of the present invention, the pH value of the composition for sterilization and cleaning is higher than pH 5 and pH 10 or lower. In another preferred embodiment of the present invention, the pH value of the composition for sterilization and cleaning is higher than pH 5 and pH 9 or lower.

In one embodiment of the present invention, the composition for sterilization and cleaning comprises 0.001% to 30% by mass of peracetic acid, 0.001% to 30% by mass of hydrogen peroxide, 1% to 70% by mass of acetic acid and/or a salt thereof, and 0.001% to 5% by mass of polyoxyethylene lauryl ether acetic acid or a salt thereof, wherein the pH value of the composition may be pH 4.0 to 10.0.

The composition for sterilization and cleaning of the present invention may comprise the peracetic acid in a concentration of 0.01% to 15% by mass, the hydrogen peroxide in a concentration of 0.01% to 25% by mass, the acetic acid and/or a salt thereof in a concentration of 1% to 60% by mass, and the polyoxyethylene lauryl ether acetic acid or a salt thereof in a concentration of 0.001% to 2% by mass, wherein the pH value of the composition may be pH 4.0 to 10.0.

The composition for sterilization and cleaning of the present invention may comprise the peracetic acid in a concentration of 0.05% to 15% by mass, the hydrogen peroxide in a concentration of 0.02% to 20% by mass, the acetic acid and/or a salt thereof in a concentration of 5% to 50% by mass, and the polyoxyethylene lauryl ether acetic acid or a salt thereof in a concentration of 0.001% to 1% by mass, wherein the pH value of the composition may be pH 4.0 to 10.0.

In one embodiment of the present invention, the above-described composition for sterilization and cleaning may further comprise a phosphorus-based stabilizer and/or a carboxylic acid-based stabilizer as an additive(s). The concentration of the phosphorus-based stabilizer and/or the carboxylic acid-based stabilizer in the composition for sterilization and cleaning of the present invention may be 0.0001% to 5% by mass.

Hereafter, individual components will be described.

(1) Polyoxyethylene Lauryl Ether Acetic Acid or a Salt Thereof

The composition for sterilization and cleaning of the present invention comprises, as an anionic surfactant, poly- oxyethylene lauryl ether acetic acid or a salt thereof. The polyoxyethylene lauryl ether acetic acid used in the composition for sterilization and cleaning of the present invention is represented by a general formula as shown below. The salt of the polyoxyethylene lauryl ether acetic acid may be, for example, a sodium salt or a potassium salt, but is not limited thereto. The polyoxyethylene lauryl ether acetic acid or a salt thereof is preferably polyoxyethylene lauryl ether acetic acid.

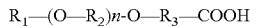

$$R_1—(O—R_2)n\text{-}O—R_3—COOH$$

In the above formula, $R_1$ represents a lauryl group, $R_2$ represents an ethylene group, $R_3$ represents a methylene group, and n represents a number of 1 to 30.

In a preferred embodiment, n may be 2 to 20. In a preferred embodiment, n may be, for example, 4, 4.5, 5, 5.5, 6, 6.5, 7, 7.5, 8, 8.5, 9, 9.5, 10, 11, 12, 13, 14, or 15, but is not limited thereto. In a more preferred embodiment, n is 4.5 or 10.

The molecular weight of the polyoxyethylene lauryl ether acetic acid or a salt thereof used in the composition for sterilization and cleaning of the present invention may be 300 to 1200. In a preferred embodiment, the molecular weight of the polyoxyethylene lauryl ether acetic acid or a salt thereof is 400 to 1000.

In the composition for sterilization and cleaning of the present invention, the concentration of the polyoxyethylene lauryl ether acetic acid or a salt thereof may be 0.001% to 5% by mass. The concentration of the polyoxyethylene lauryl ether acetic acid or a salt thereof may be preferably 0.001% to 2% by mass, and more preferably 0.001% to 1% by mass.

(2) Other Components

Hydrogen Peroxide

The composition for sterilization and cleaning of the present invention comprises hydrogen peroxide. In the composition for sterilization and cleaning of the present invention, since hydrogen peroxide itself has sterilizing and/or cleaning ability, the hydrogen peroxide does not only contribute to the enhancement of the sterilizing and/or cleaning effects of the composition as a whole, but also contributes to generation and maintenance of a sufficient amount of peracetic acid as a result of an equilibrium reaction with acetic acid (stability in an aqueous solution).

Accordingly, by the combination of acetic acid with hydrogen peroxide, the sterilizing and/or cleaning effects of the composition of the present invention can be further enhanced.

The concentration of the hydrogen peroxide in the composition for sterilization and cleaning of the present invention is preferably 0.001% to 30% by mass, more preferably 0.01% to 25% by mass, and further preferably 0.02% to 20% by mass. If the concentration of the hydrogen peroxide is too low, the amount of peracetic acid generated as a result of an equilibrium reaction with acetic acid is not sufficient, and the sterilizing and/or cleaning effects of the present invention are not sufficiently exhibited in some cases. On the other hand, even if the concentration of the hydrogen peroxide is too high, the above-described effects are not increased, and rather, it causes problem in terms of safety in some cases.

Acetic Acid and/or Salt Thereof

The acetic acid and/or a salt thereof used in the composition for sterilization and cleaning of the present invention may be those commonly used in the present technical field.

The concentration of the acetic acid and/or a salt thereof in the composition for sterilization and cleaning of the present invention may be preferably 1% to 70% by mass, more preferably 1% to 60% by mass, and further preferably 5% to 50% by mass.

Peracetic Acid

The peracetic acid used in the composition for sterilization and cleaning of the present invention may be those commonly used in the present technical field.

The concentration of the peracetic acid in the composition for sterilization and cleaning of the present invention may be preferably 0.001% to 30% by mass, more preferably 0.01% to 15% by mass, and further preferably 0.05% to 15% by mass.

Stabilizer(s)

The composition for sterilization and cleaning of the present invention may comprise a stabilizer(s) as an additive(s). By adding a stabilizer(s) to the present composition for sterilization and cleaning, the stability of hydrogen peroxide is improved. Any stabilizer can be used, as long as it is a stabilizer for hydrogen peroxide. For example, a phosphorus-based stabilizer and/or a carboxylic acid-based stabilizer can be used. Examples of the phosphorus-based stabilizer that can be used in the composition for sterilization and cleaning of the present invention may include pyrophosphoric acid or a salt thereof, phosphoric acid or a salt thereof, 1-hydroxyethylidene-1,1-diphosphonic acid (HEDP) or a salt thereof, diethylenetriamine penta(methylene phosphonic acid) (DTPP) or a salt thereof, nitrilotris(methylenephosphonic acid) or a salt thereof, 2-phosphonobutane-1,2,4-tricarboxylic acid or a salt thereof, and ethylenediamine tetra(methylene phosphonic acid) or a salt thereof, but the examples are not limited thereto. The phosphorus-based stabilizer is preferably 1-hydroxyethylidene-1,1-diphosphonic acid (HEDP) or a salt thereof. Examples of the carboxylic acid-based stabilizer that can be used in the composition for sterilization and cleaning of the present invention may include ethylenediaminetetraacetic acid (EDTA) or a salt thereof, diethylenetriamine pentaacetic acid (DTPA) or a salt thereof, picolinic acid or a salt thereof, dipicolinic acid or a salt thereof, nitrilotriacetic acid or a salt thereof, N-(2-hydroxyethyl)ethylenediamine-N,N', N''-triacetic acid or a salt thereof, triethylenetetramine-N,N,N',N'',N''',N'''-hexaacetic acid or a salt thereof, 1,3-propanediamine-N,N,N',N'-tetraacetic acid, 1,3-diamino-2-propanol-N,N,N',N'-tetraacetic acid, N-(2-hydroxyethyl)iminodiacetic acid or a salt thereof, N,N-di(2-hydroxyethyl)glycine or a salt thereof, glycol ether diamine tetraacetic acid, and (S,S)-ethylenediamine-N,N'-disuccinic acid or a salt thereof, but the examples are not limited thereto. The carboxylic acid-based stabilizer is preferably ethylenediaminetetraacetic acid (EDTA) or a salt thereof.

The concentration of the stabilizer(s) in the composition for sterilization and cleaning of the present invention may be preferably 0.0001% to 5% by mass, more preferably 0.0001% to 2% by mass, and further preferably 0.0002% to 1% by mass.

Other Components

The composition for sterilization and cleaning of the present invention may further comprise, as necessary, additives used in common drugs for sterilization and cleaning, etc., such as, for example, surfactants, thickeners, flavors, coloring agents, and hydrolases, as appropriate. In the composition for sterilization and cleaning of the present invention, the balance other than the polyoxyethylene lauryl ether acetic acid or a salt thereof, the hydrogen peroxide, the acetic acid, the peracetic acid, and the additives added as necessary, such as stabilizers, is mainly water.

The composition for sterilization and cleaning of the present invention may be directly used without being diluted, or it may be diluted to any given concentration and may be used as a diluted composition for sterilization and cleaning. As a diluent, water is generally used. Such water used as a diluent may be, for example, pure water, ultrapure water, distilled water, purified water, water for injection, and tap water. The dilution magnification is not particularly limited, as long as it may be a dilution magnification capable of preparing a concentration that exhibits the sterilizing and cleaning effects of a diluted composition for sterilization and cleaning. The dilution magnification is preferably 1 to 10000 times, and more preferably 1 to 1000 times.

A-2. Diluted Composition for Sterilization and Cleaning

The diluted composition for sterilization and cleaning of the present invention comprises peracetic acid, hydrogen peroxide, acetic acid and/or a salt thereof, polyoxyethylene lauryl ether acetic acid or a salt thereof, water, and additional water used as a diluent. Individual components are as mentioned above.

The diluted composition for sterilization and cleaning of the present invention may be prepared by diluting the above-described composition for sterilization and cleaning with water. As described above, the dilution magnification is not particularly limited, as long as it may be a dilution magnification capable of preparing a concentration that exhibits the sterilizing and cleaning effects of a diluted composition for sterilization and cleaning. The dilution magnification is preferably 1 to 10000 times, and more preferably 1 to 1000 times.

In one embodiment of the present invention, the diluted composition for sterilization and cleaning may comprise 0.001% to 1.5% by mass of peracetic acid, 0.001% to 2.5% by mass of hydrogen peroxide, 0.01% to 7% by mass of acetic acid and/or a salt thereof, and 0.00001% to 0.1% by mass of polyoxyethylene lauryl ether acetic acid or a salt thereof.

The diluted composition for sterilization and cleaning of the present invention may comprise the peracetic acid in a concentration of 0.001% to 0.5% by mass, the hydrogen peroxide in a concentration of 0.005% to 1% by mass, the acetic acid and/or a salt thereof in a concentration of 0.05% to 5% by mass, and the polyoxyethylene lauryl ether acetic acid or a salt thereof in a concentration of 0.00005% to 0.05% by mass.

A-3. Methods for Producing a Composition for Sterilization and Cleaning and a Diluted Composition for Sterilization and Cleaning In one embodiment of the present invention, a method for producing a composition for sterilization and cleaning may comprise a mixing step of mixing at least the following components:

(i) a hydrogen peroxide solution;
(ii) acetic acid; and (iii) polyoxyethylene lauryl ether acetic acid or a salt thereof.

When the aqueous solution reaches an equilibrium state, peracetic acid appears to be also present in the aqueous solution. However, in the mixing step, peracetic acid may also be added. Individual components are as mentioned above. The order of mixing individual components may be arbitrary, and in the composition for sterilization and cleaning of the present invention, the mixed individual components are in an equilibrium state.

In one embodiment of the present invention, a method for producing a composition for sterilization and cleaning may comprise a mixing step of mixing at least the following components:
(i) a phosphorus-based stabilizer and/or a carboxylic acid-based stabilizer used as an additive(s);
(ii) a hydrogen peroxide solution and acetic acid;
(iii) acetate; and
(iv) polyoxyethylene lauryl ether acetic acid or a salt thereof.

The above-described acetate may be an acetate that is alkaline when it is processed into an aqueous solution. Examples of the acetate that can be used herein may include sodium acetate, potassium acetate, lithium acetate, beryllium acetate, magnesium acetate, aluminum acetate, calcium acetate, rubidium acetate, strontium acetate, cesium acetate, barium acetate, and ammonium acetate, but the examples are not limited thereto. In one embodiment of the present invention, the acetate may be sodium acetate. In another embodiment of the present invention, the acetate may be potassium acetate.

In one embodiment of the present invention, a method for producing a composition for sterilization and cleaning may comprise a mixing step of mixing at least the following components:
(i) a phosphorus-based stabilizer and/or a carboxylic acid-based stabilizer used as an additive(s);
(ii) a hydrogen peroxide solution and acetic acid;
(iii) alkali; and
(iv) polyoxyethylene lauryl ether acetic acid or a salt thereof.

In this production method, a heat of neutralization is generated, and a transition speed increases, so that the reaction may be accelerated. When the aqueous solution has reached an equilibrium state, peracetic acid appears to be also present in the aqueous solution. However, in the mixing step, peracetic acid may also be added. Individual components are as mentioned above. The order of mixing individual components may be arbitrary, and in the composition for sterilization and cleaning of the present invention, the mixed individual components are in an equilibrium state.

Examples of the above-described alkali that can be used herein may include sodium hydroxide, potassium hydroxide, lithium hydroxide, beryllium hydroxide, magnesium hydroxide, aluminum hydroxide, calcium hydroxide, rubidium hydroxide, strontium hydroxide, cesium hydroxide, barium hydroxide, and ammonia, but the examples are not limited thereto. In one embodiment of the present invention, the alkali may be sodium hydroxide. In another embodiment of the present invention, the alkali may be potassium hydroxide.

In one embodiment of the present invention, a method for producing a composition for sterilization and cleaning may comprise a mixing step of mixing at least the following components:
(i) an additive;
(ii) a hydrogen peroxide solution and acetic acid;
(iii) one or more selected from a phosphate, a citrate, and a tris base; and
(iv) polyoxyethylene lauryl ether acetic acid or a salt thereof.

By adding one or more selected from a phosphate, a citrate, and a tris base to the composition, a change in the pH value after dilution can be further reduced. In this production method, when a phosphate or a citrate is used as a component (iii), a heat of neutralization is not generated, and good workability is obtained. On the other hand, in this production method, when a tris base is used as a component (iii), a heat of neutralization is generated, and a transition speed increases, so that the reaction may be accelerated. When the aqueous solution has reached an equilibrium state, peracetic acid appears to be also present in the aqueous solution. However, in the mixing step, peracetic acid may also be added. Individual components are as mentioned above. The order of mixing individual components may be arbitrary, and in the composition for sterilization and cleaning of the present invention, the mixed individual components are in an equilibrium state.

Examples of the above-described phosphate may include a sodium salt of phosphoric acid and a potassium salt of phosphoric acid, but the examples are not limited thereto. Examples of such a sodium salt of phosphoric acid may include sodium dihydrogen phosphate, disodium hydrogen phosphate, and trisodium phosphate, but the examples are not limited thereto. Examples of such a potassium salt of phosphoric acid may include potassium dihydrogen phosphate, dipotassium hydrogen phosphate, and tripotassium phosphate, but the examples are not limited thereto.

The above-described tris base means tris(hydroxymethyl) aminomethane.

The above-described production method using an alkali or a tris base may comprise, after completion of the mixing of an additive, acetic acid, an alkali or a tris base, and polyoxyethylene lauryl ether acetic acid or a salt thereof, a step of mixing a hydrogen peroxide solution with the mixture at 30° C. to 50° C. In this production method, a heat of neutralization is generated. Thus, by utilizing such a heat of neutralization generated as a result of the mixing of an additive, acetic acid, and an alkali or a tris base, a hydrogen peroxide solution can be mixed with the mixture at 30° C. to 50° C., and a transition speed thereby increases, so that the reaction can be accelerated.

In one embodiment of the present invention, a method for producing a composition for sterilization and cleaning may comprise the following steps (A) and (B):
a step (A) of mixing, at least, (i) an additive, (ii) a hydrogen peroxide solution and acetic acid, (iii) acetate, or alkali, or one or more selected from a phosphate, a citrate, and a tris base, and (iv) polyoxyethylene lauryl ether acetic acid or a salt thereof; and
a step (B) of leaving an aqueous solution (a) obtained in the step (A) at rest for 1 day or more.

The aqueous solution (a) obtained in the step (A) is left at rest in the step (B), so that the aqueous solution reaches an equilibrium state. In an embodiment of using an acetate, a phosphate, or a citrate, the temperature, at which the aqueous solution is left at rest in the step (B), is preferably 20° C. to 60° C., and more preferably 20° C. to 50° C. In addition, the time, in which the aqueous solution is left at rest in the step (B), is preferably 1 day or more, and it may be, for example, 2 days or more, 3 days or more, 5 days or more, 10 days or more, 30 days or more, etc. In an embodiment of using an alkali or a tris base, as described above, the reaction can be accelerated as a result of generation of a heat of neutralization.

In a further embodiment of the present invention, a method for producing a composition for sterilization and cleaning may comprise the following steps (C) to (E):
- a step (C) of mixing, at least, (ii) a hydrogen peroxide solution and acetic acid and (i) an additive;
- a step (D) of leaving an aqueous solution (c) obtained in the step (C) at rest for 1 day or more; and
- a step (E) of mixing an aqueous solution (d) obtained in the step (D), (iii) acetate, or alkali, or one or more selected from a phosphate, a citrate, and a tris base, (iv) polyoxyethylene lauryl ether acetic acid or a salt thereof, and water.

By leaving the aqueous solution (c) obtained in the step (C) at rest, the aqueous solution reaches an equilibrium state. The temperature, at which the aqueous solution is left at rest in the step (D), is preferably 20° C. to 60° C., and more preferably 20° C. to 50° C. In addition, the time, in which the aqueous solution is left at rest in the step (D), is preferably 1 day or more, and it may be, for example, 2 days or more, 3 days or more, 5 days or more, 10 days or more, 30 days or more, etc. Thereafter, acetate, or alkali, or one or more selected from a phosphate, a citrate, and a tris base, and water are mixed with the aqueous solution (d) that has reached an equilibrium state.

In one embodiment of the present invention, a method for producing a diluted composition for sterilization and cleaning may comprise, a mixing step of mixing at least the following components:
- (i) a phosphorus-based stabilizer and/or a carboxylic acid-based stabilizer as an additive(s);
- (ii) a hydrogen peroxide solution and acetic acid;
- (iii) acetate, or alkali, or one or more selected from a phosphate, a citrate, and a tris base; and
- (iv) polyoxyethylene lauryl ether acetic acid or a salt thereof, and a dilution step of diluting the obtained mixed solution.

When the aqueous solution has reached an equilibrium state, peracetic acid appears to be also present in the aqueous solution. However, in the mixing step, peracetic acid may also be added. Individual components are as mentioned above. In the method for producing a diluted composition for sterilization and cleaning of the present invention, the dilution step may comprise mixing the mixture obtained in the mixing step with water. The water used as a diluent may be, for example, pure water, ultrapure water, distilled water, purified water, water for injection, or tap water.

Embodiment B

B-1. Composition for Sterilization and Cleaning

The composition for sterilization and cleaning of the present invention comprises peracetic acid, hydrogen peroxide, acetic acid and/or a salt thereof, polyoxyethylene lauryl ether acetic acid or a salt thereof, and water.

In one embodiment of the present invention, the composition for sterilization and cleaning may comprise 0.01% to 30% by mass of peracetic acid, 0.1% to 30% by mass of hydrogen peroxide, 1% to 60% by mass of acetic acid, and 0.001% to 5% by mass of polyoxyethylene lauryl ether acetic acid or a salt thereof.

The composition for sterilization and cleaning of the present invention may comprise the peracetic acid in a concentration of 0.1% to 15% by mass, the hydrogen peroxide in a concentration of 1% to 25% by mass, the acetic acid in a concentration of 1% to 50% by mass, and the polyoxyethylene lauryl ether acetic acid or a salt thereof in a concentration of 0.001% to 2% by mass.

The composition for sterilization and cleaning of the present invention may comprise the peracetic acid in a concentration of 0.5% to 15% by mass, the hydrogen peroxide in a concentration of 2% to 20% by mass, the acetic acid in a concentration of 5% to 50% by mass, and the polyoxyethylene lauryl ether acetic acid or a salt thereof in a concentration of 0.001% to 1% by mass.

Hereafter, individual components will be described.

(1) Polyoxyethylene Lauryl Ether Acetic Acid or a Salt Thereof

The composition for sterilization and cleaning of the present invention comprises, as an anionic surfactant, polyoxyethylene lauryl ether acetic acid or a salt thereof. The polyoxyethylene lauryl ether acetic acid used in the composition for sterilization and cleaning of the present invention is represented by a general formula as shown below. The salt of the polyoxyethylene lauryl ether acetic acid may be, for example, a sodium salt or a potassium salt, but is not limited thereto. The polyoxyethylene lauryl ether acetic acid or a salt thereof is preferably polyoxyethylene lauryl ether acetic acid.

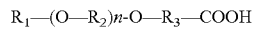

$R_1-(O-R_2)n-O-R_3-COOH$

In the above formula, $R_1$ represents a lauryl group, $R_2$ represents an ethylene group, $R_3$ represents a methylene group, and n represents a number of 1 to 30.

In a preferred embodiment, n may be 2 to 20. In a preferred embodiment, n may be, for example, 4, 4.5, 5, 5.5, 6, 6.5, 7, 7.5, 8, 8.5, 9, 9.5, 10, 11, 12, 13, 14, or 15, but is not limited thereto. In a more preferred embodiment, n is 4.5 or 10.

The molecular weight of the polyoxyethylene lauryl ether acetic acid or a salt thereof used in the composition for sterilization and cleaning of the present invention may be 300 to 1200. In a preferred embodiment, the molecular weight of the polyoxyethylene lauryl ether acetic acid or a salt thereof is 400 to 1000.

In the composition for sterilization and cleaning of the present invention, the concentration of the polyoxyethylene lauryl ether acetic acid or a salt thereof may be 0.001% to 5% by mass. The concentration of the polyoxyethylene lauryl ether acetic acid or a salt thereof may be preferably 0.001% to 2% by mass, and more preferably 0.001% to 1% by mass. In one embodiment of the present invention, the concentration of the polyoxyethylene lauryl ether acetic acid or a salt thereof may be 0.01% to 5% by mass, 0.01% to 2% by mass, 0.01% to 1% by mass, or the like.

(2) Other Components

Hydrogen Peroxide

The composition for sterilization and cleaning of the present invention comprises hydrogen peroxide. In the composition for sterilization and cleaning of the present invention, since hydrogen peroxide itself has sterilizing and/or cleaning ability, the hydrogen peroxide does not only contribute to the enhancement of the sterilizing and/or cleaning effects of the composition as a whole, but also contributes to generation and maintenance of a sufficient amount of peracetic acid as a result of an equilibrium reaction with acetic acid (stability in an aqueous solution). Accordingly, by the combination of acetic acid with hydrogen peroxide, the sterilizing and/or cleaning effects of the composition of the present invention can be further enhanced.

The concentration of the hydrogen peroxide in the composition for sterilization and cleaning of the present invention is preferably 0.1% to 30% by mass, more preferably 1% to 25% by mass, and further preferably 2% to 20% by mass. If the concentration of the hydrogen peroxide is too low, the amount of peracetic acid generated as a result of an equilibrium reaction with acetic acid is not sufficient, and the sterilizing and/or cleaning effects of the present invention are not sufficiently exhibited in some cases. On the other hand, even if the concentration of the hydrogen peroxide is too high, the above-described effects are not increased, and rather, it causes problem in terms of safety in some cases.

Acetic Acid

The acetic acid used in the composition for sterilization and cleaning of the present invention may be those commonly used in the present technical field.

The concentration of the acetic acid in the composition for sterilization and cleaning of the present invention may be preferably 1% to 60% by mass, more preferably 1% to 50% by mass, and further preferably 5% to 50% by mass.

Peracetic Acid

The peracetic acid used in the composition for sterilization and cleaning of the present invention may be those commonly used in the present technical field.

The concentration of the peracetic acid in the composition for sterilization and cleaning of the present invention may be preferably 0.01% to 30% by mass, more preferably 0.1% to 15% by mass, and further preferably 0.5% to 15% by mass.

Stabilizer

The composition for sterilization and cleaning of the present invention may comprise a stabilizer. By adding a stabilizer to the present composition for sterilization and cleaning, the stability of hydrogen peroxide is improved. Any stabilizer can be used, as long as it is a stabilizer for hydrogen peroxide. For example, a phosphorus-based stabilizer can be used. Examples of the phosphorus-based stabilizer that can be used in the composition for sterilization and cleaning of the present invention may include pyrophosphoric acid, phosphoric acid, 1-hydroxyethylidene-1,1-diphosphonic acid (HEDP), nitrilotris(methylenephosphonic acid), 2-phosphonobutane-1,2,4-tricarboxylic acid, and ethylenediamine tetra(methylene phosphonic acid), but the examples are not limited thereto. The phosphorus-based stabilizer is preferably pyrophosphoric acid.

The concentration of the stabilizer in the composition for sterilization and cleaning of the present invention may be preferably 0.01% to 5% by mass, more preferably 0.01% to 2% by mass, and further preferably 0.02% to 1% by mass.

Chelating Agent

The composition for sterilization and cleaning of the present invention may comprise a chelating agent. By allowing the present composition for sterilization and cleaning to comprise such a chelating agent, effects such as suppression of scale generation, scale removal, and protein removal are improved. The chelating agent that can be used in the composition for sterilization and cleaning of the present invention may include ethylenediaminetetraacetic acid, citric acid, malic acid, 1-hydroxyethylidene-1,1-diphosphonic acid (HEDP), and dipicolinic acid, but the examples are not limited thereto. The chelating agent is preferably dipicolinic acid.

Other Components

The composition for sterilization and cleaning of the present invention may further comprise, as necessary, additives used in common drugs for sterilization and cleaning, etc., such as, for example, surfactants, thickeners, flavors, coloring agents, and hydrolases, as appropriate. In the composition for sterilization and cleaning of the present invention, the balance other than the polyoxyethylene lauryl ether acetic acid or a salt thereof, the hydrogen peroxide, the acetic acid, the peracetic acid, and additives added as necessary, such as a stabilizer, is mainly water.

The pH value of the composition for sterilization and cleaning of the present invention is pH 7 or lower, and preferably pH 5 or lower. If the pH value exceeds pH 7, there is a case where hydrogen peroxide and peracetic acid are decomposed, and stability is decreased.

The composition for sterilization and cleaning of the present invention may be directly used without being diluted, or it may be diluted to any given concentration and may be used as a diluted composition for sterilization and cleaning. As a diluent, water is generally used. Such water used as a diluent may be, for example, pure water, ultrapure water, distilled water, purified water, water for injection, and tap water. The dilution magnification is not particularly limited, as long as it may be a dilution magnification capable of preparing a concentration that exhibits the sterilizing and cleaning effects of a diluted composition for sterilization and cleaning. The dilution magnification is preferably 1 to 10000 times, and more preferably 1 to 1000 times.

B-2. Diluted Composition for Sterilization and Cleaning

The diluted composition for sterilization and cleaning of the present invention comprises peracetic acid, hydrogen peroxide, acetic acid, polyoxyethylene lauryl ether acetic acid or a salt thereof, water, and additional water used as a diluent. Individual components are as mentioned above.

The diluted composition for sterilization and cleaning of the present invention may be prepared by diluting the above-described composition for sterilization and cleaning with water. As described above, the dilution magnification is not particularly limited, as long as it may be a dilution magnification capable of preparing a concentration that exhibits the sterilizing and cleaning effects of a diluted composition for sterilization and cleaning. The dilution magnification is preferably 1 to 10000 times, and more preferably 1 to 1000 times.

In one embodiment of the present invention, the diluted composition for sterilization and cleaning may comprise 0.001% to 0.2% by mass of peracetic acid, 0.01% to 2% by mass of hydrogen peroxide, 0.01% to 1% by mass of acetic acid, and 0.00001% to 0.1% by mass of polyoxyethylene lauryl ether acetic acid or a salt thereof.

The diluted composition for sterilization and cleaning of the present invention may comprise the peracetic acid in a concentration of 0.005% to 0.1% by mass, the hydrogen peroxide in a concentration of 0.01% to 1% by mass, the acetic acid in a concentration of 0.05% to 0.5% by mass, and the polyoxyethylene lauryl ether acetic acid or a salt thereof in a concentration of 0.0001% to 0.1% by mass.

B-3. Methods for Producing a Composition for Sterilization and Cleaning and a Diluted Composition for Sterilization and Cleaning In one embodiment of the present invention, a method for producing a composition for sterilization and cleaning may comprise a mixing step of mixing at least the following components:
(i) a hydrogen peroxide solution;
(ii) acetic acid; and
(iii) polyoxyethylene lauryl ether acetic acid or a salt thereof.

When the aqueous solution reaches an equilibrium state, peracetic acid appears to be also present in the aqueous solution. However, in the mixing step, peracetic acid may also be added. Individual components are as mentioned above. The order of mixing individual components may be arbitrary, and in the composition for sterilization and cleaning of the present invention, the mixed individual components are in an equilibrium state.

In another embodiment of the present invention, a method for producing a composition for sterilization and cleaning may comprise the following steps (A) and (B):
a step (A) of mixing, at least, acetic acid, 30% to 65% by mass of a hydrogen peroxide aqueous solution, and polyoxyethylene lauryl ether acetic acid or a salt thereof; and
a step (B) of leaving an aqueous solution (a) obtained in the step (A) at rest at 20° C. to 60° C. for 1 day or more.

The aqueous solution (a) obtained in the step (A) is left at rest in the step (B), so that the aqueous solution reaches an equilibrium state. The temperature, at which the aqueous solution is left at rest in the step (B), is preferably 20° C. to 60° C., and more preferably 20° C. to 50° C. In addition, the time, in which the aqueous solution is left at rest in the step (B), is preferably 1 day or more, and it may be, for example, 2 days or more, 3 days or more, 5 days or more, 10 days or more, 30 days or more, etc. In the production method of the composition for sterilization and cleaning of the present invention, the step (A) may further comprise mixing a chelating agent into the mixture. The chelating agent is as mentioned above.

In a further embodiment of the present invention, a method for producing a composition for sterilization and cleaning may comprise the following steps (C) to (E):
a step (C) of mixing, at least, acetic acid and 30% to 65% by mass of a hydrogen peroxide aqueous solution;
a step (D) of leaving an aqueous solution (c) obtained in the step (C) at rest at 20° C. to 60° C. for 1 day or more; and
a step (E) of mixing an aqueous solution (d) obtained in the step (D), polyoxyethylene lauryl ether acetic acid or a salt thereof, and water.

By leaving the aqueous solution (c) obtained in the step (C) at rest, the aqueous solution reaches an equilibrium state. The temperature, at which the aqueous solution is left at rest in the step (D), is preferably 20° C. to 60° C., and more preferably 20° C. to 50° C. In addition, the time, in which the aqueous solution is left at rest in the step (D), is preferably 1 day or more, and it may be, for example, 2 days or more, 3 days or more, 5 days or more, 10 days or more, 30 days or more, etc. Thereafter, polyoxyethylene lauryl ether acetic acid or a salt thereof, and water are mixed with the aqueous solution (d) that has reached an equilibrium state. In the composition for sterilization and cleaning of the present invention, the mixed individual components are in an equilibrium state. In the production method of the composition for sterilization and cleaning of the present invention, the step (E) may further comprise mixing a chelating agent into the mixture. The chelating agent is as mentioned above.

In one embodiment of the present invention, a method for producing a diluted composition for sterilization and cleaning may comprise,
a mixing step of mixing at least the following components:
(i) a hydrogen peroxide solution;
(ii) acetic acid; and
(iii) polyoxyethylene lauryl ether acetic acid or a salt thereof, and
a dilution step of diluting the obtained mixed solution.

When the aqueous solution has reached an equilibrium state, peracetic acid appears to be also present in the aqueous solution. However, in the mixing step, peracetic acid may also be added. Individual components are as mentioned above. In the method for producing a diluted composition for sterilization and cleaning of the present invention, the dilution step may comprise mixing the mixture obtained in the mixing step with water. The water used as a diluent may be, for example, pure water, ultrapure water, distilled water, purified water, water for injection, or tap water. In the diluted composition for sterilization and cleaning of the present invention, the mixed individual components are in an equilibrium state.

Embodiment C

C-1. Composition for Sterilization and Cleaning

In one embodiment of the present invention, the composition for sterilization and cleaning comprises peracetic acid, hydrogen peroxide, acetic acid and/or a salt thereof, water, and a phosphorus-based stabilizer and/or a carboxylic acid-based stabilizer as an additive(s).

In one embodiment of the present invention, the pH value of the composition for sterilization and cleaning may be pH 4.0 to 10.0. In one embodiment of the present invention, the pH value of the composition for sterilization and cleaning may be, for example, pH 4.0, 4.5, 5.0, 5.1, 5.2, 5.3, 5.4, 5.5, 5.6, 5.7, 5.8, 5.9, 6.0, 6.5, 7.0, 7.5, 8.0, 8.5, 9.0, 9.5, 10.0 or the like, but it is not limited to these values. In one embodiment of the present invention, the pH value of the composition for sterilization and cleaning may be, for example, pH 4.0 to 10.0, 4.0 to 9.5, 4.0 to 9.0, 4.0 to 8.5, 4.0 to 8.0, 4.0 to 7.5, 4.0 to 7.0, 4.0 to 6.5, or 4.0 to 6.0. In one embodiment of the present invention, the pH value of the composition for sterilization and cleaning may be pH 4.5 to 10.0, 4.5 to 9.5, 4.5 to 9.0, 4.5 to 8.5, 4.5 to 8.0, 4.5 to 7.5, 4.5 to 7.0, 4.5 to 6.5, or 4.5 to 6.0. In one embodiment of the present invention, the pH value of the composition for sterilization and cleaning may be pH 5.0 to 10.0, 5.0 to 9.5, 5.0 to 9.0, 5.0 to 8.5, 5.0 to 8.0, 5.0 to 7.5, 5.0 to 7.0, 5.0 to 6.5, or 5.0 to 6.0. In one embodiment of the present invention, the pH value of the composition for sterilization and cleaning may be pH 5.1 to 10.0, 5.1 to 9.5, 5.1 to 9.0, 5.1 to 8.5, 5.1 to 8.0, 5.1 to 7.5, 5.1 to 7.0, 5.1 to 6.5, or 5.1 to 6.0. In one embodiment of the present invention, the pH value of the composition for sterilization and cleaning may be pH 5.2 to 10.0, 5.2 to 9.5, 5.2 to 9.0, 5.2 to 8.5, 5.2 to 8.0, 5.2 to 7.5, 5.2 to 7.0, 5.2 to 6.5, or 5.2 to 6.0. In one embodiment of the present invention, the pH value of the composition for sterilization and cleaning may be pH 5.3 to 10.0, 5.3 to 9.5, 5.3 to 9.0, 5.3 to 8.5, 5.3 to 8.0, 5.3 to 7.5, 5.3 to 7.0, 5.3 to 6.5, or 5.3 to 6.0. In one embodiment of the present invention, the pH value of the composition for sterilization and cleaning may be pH 5.4 to 10.0, 5.4 to 9.5, 5.4 to 9.0, 5.4 to 8.5, 5.4 to 8.0, 5.4 to 7.5, 5.4 to 7.0, 5.4 to 6.5, or 5.4 to 6.0. In one embodiment of the present invention, the pH value of the composition for sterilization and cleaning may be pH 5.5 to 10.0, 5.5 to 9.5, 5.5 to 9.0, 5.5 to 8.5, 5.5 to 8.0, 5.5 to 7.5, 5.5 to 7.0, 5.5 to 6.5, or 5.5 to 6.0. Ina preferred embodiment of the present invention, the pH value of the composition for sterilization and cleaning is higher than pH 5.0. In a preferred embodiment of the present invention, the pH value of the composition for sterilization and cleaning is higher than pH 5 and pH 10 or lower. In another preferred embodiment of the present invention, the pH value of the composition for sterilization and cleaning is higher than pH 5 and pH 9 or lower.

In one embodiment of the present invention, the composition for sterilization and cleaning comprises 0.001% to 15% by mass of peracetic acid, 0.01% to 70% by mass of acetic acid and/or a salt thereof, 0.001% to 25% by mass of hydrogen peroxide, and water, and also comprises, as an additive(s), a phosphorus-based stabilizer and/or a carboxylic acid-based stabilizer, wherein the pH value of the composition may be pH 4.0 to 10.0.

In one embodiment of the present invention, the above-described composition for sterilization and cleaning may further comprise one or more selected from a phosphate, a citrate, and a tris base. In the composition for sterilization and cleaning of the present invention, the concentration of one or more selected from a phosphate, a citrate, and a tris base may be 0.01% to 70% by mass.

In one embodiment of the present invention, the above-described composition for sterilization and cleaning may further comprise sodium stannate. In the composition for sterilization and cleaning of the present invention, the concentration of the sodium stannate may be 0.0001% to 5% by mass.

In another embodiment of the present invention, the composition for sterilization and cleaning comprises 0.001% to 15% by mass of peracetic acid, 0.01% to 70% by mass of acetic acid and/or a salt thereof, 0.001% to 25% by mass of hydrogen peroxide, and water, and also comprises sodium stannate as an additive, wherein the pH value of the composition may be pH 4.0 to 10.0.

In the composition for sterilization and cleaning of the present invention, the concentration of the sodium stannate may be 0.0001% to 5% by mass.

In one embodiment of the present invention, the above-described composition for sterilization and cleaning may further comprise a phosphorus-based stabilizer and/or a carboxylic acid-based stabilizer. In the composition for sterilization and cleaning of the present invention, the concentration of the phosphorus-based stabilizer may be 0.0001% by mass or more and less than 0.5% by mass, and the concentration of the carboxylic acid-based stabilizer may be 0.0001% by mass or more and less than 0.5% by mass.

Hereafter, individual components will be described.

(1) Additives (1-1) Stabilizers

The composition for sterilization and cleaning of the present invention comprises peracetic acid, hydrogen peroxide, acetic acid and/or a salt thereof, and water, and may also comprise a phosphorus-based stabilizer and/or a carboxylic acid-based stabilizer as an additive(s). By addition of these stabilizers, the stability of the hydrogen peroxide is improved, and the pH value of the composition for sterilization and cleaning can be adjusted to pH 4.0 to 10.0. The composition for sterilization and cleaning of the present invention may comprise only a phosphorus-based stabilizer and/or a carboxylic acid-based stabilizer as an additive(s), or may comprise these stabilizers in combination with sodium stannate. In addition, the composition for sterilization and cleaning of the present invention may further comprise, as an additive(s), one or more selected from a phosphate, a citrate, and a tris base.

Phosphorus-Based Stabilizer

The composition for sterilization and cleaning of the present invention may comprise a phosphorus-based stabilizer as an additive. The type of the phosphorus-based stabilizer is not particularly limited, as long as it stabilizes hydrogen peroxide and can adjust the pH value of the composition for sterilization and cleaning within the above-described range by addition thereof together with a carboxylic acid-based stabilizer. Examples of the phosphorus-based stabilizer that can be used in the composition for sterilization and cleaning of the present invention may include pyrophosphoric acid or a salt thereof, phosphoric acid or a salt thereof, 1-hydroxyethylidene-1,1-diphosphonic acid (HEDP) or a salt thereof, diethylenetriamine penta (methylene phosphonic acid) (DTPP) or a salt thereof, nitrilotris(methylenephosphonic acid) or a salt thereof, 2-phosphonobutane-1,2,4-tricarboxylic acid or a salt thereof, and ethylenediamine tetra(methylene phosphonic acid) or a salt thereof, but the examples are not limited thereto. In one embodiment of the present invention, the phosphorus-based stabilizer may be 1-hydroxyethylidene-1,1-diphosphonic acid (HEDP) or a salt thereof. In another embodiment of the present invention, the phosphorus-based stabilizer may be diethylenetriamine penta(methylene phosphonic acid) (DTPP) or a salt thereof. In a further embodiment of the present invention, the phosphorus-based stabilizer may be pyrophosphoric acid or a salt thereof. In a preferred embodiment of the present invention, the phosphorus-based stabilizer may be 1-hydroxyethylidene-1,1-diphosphonic acid (HEDP) or a salt thereof.

In the composition for sterilization and cleaning of the present invention, the concentration of the phosphorus-based stabilizer may be 0.0001% by mass or more and less than 0.5% by mass, preferably 0.0001% to 0.30% by mass, more preferably 0.0001% to 0.20% by mass, and further preferably 0.0001% to 0.10% by mass.

Carboxylic Acid-Based Stabilizer

The composition for sterilization and cleaning of the present invention may comprise a carboxylic acid-based stabilizer as an additive. The type of the carboxylic acid-based stabilizer is not particularly limited, as long as it stabilizes hydrogen peroxide and can adjust the pH value of the composition for sterilization and cleaning within the above-described range by addition thereof together with a phosphorus-based stabilizer. Examples of the carboxylic acid-based stabilizer that can be used in the composition for sterilization and cleaning of the present invention may include ethylenediaminetetraacetic acid (EDTA) or a salt thereof, diethylenetriamine pentaacetic acid (DTPA) or a salt thereof, picolinic acid or a salt thereof, dipicolinic acid or a salt thereof, nitrilotriacetic acid or a salt thereof, N-(2-hydroxyethyl)ethylenediamine-N,N',N''-triacetic acid or a salt thereof, triethylenetetramine-N,N,N',N'',N''',N'''-hexaacetic acid or a salt thereof, 1,3-propanediamine-N,N,N',N'-tetraacetic acid, 1,3-diamino-2-propanol-N,N,N',N'-tetraacetic acid, N-(2-hydroxyethyl)iminodiacetic acid or a salt thereof, N,N-di(2-hydroxyethyl)glycine or a salt thereof, glycol ether diamine tetraacetic acid, and (S,S)-ethylenediamine-N,N'-disuccinic acid or a salt thereof, but the examples are not limited thereto. In one embodiment of the present invention, the carboxylic acid-based stabilizer may be ethylenediaminetetraacetic acid (EDTA) or a salt thereof. In another embodiment of the present invention, the carboxylic acid-based stabilizer may be diethylenetriamine pentaacetic acid (DTPA) or a salt thereof. In a preferred embodiment of the present invention, the carboxylic acid-based stabilizer may be ethylenediaminetetraacetic acid (EDTA) or a salt thereof.

In the composition for sterilization and cleaning of the present invention, the concentration of the carboxylic acid-based stabilizer may be 0.0001% by mass or more and less than 0.5% by mass, preferably 0.0001% to 0.30% by mass, more preferably 0.0001% to 0.20% by mass, and further preferably 0.0001% to 0.10% by mass.

In one embodiment of the present invention, the composition for sterilization and cleaning may comprise:
  as a phosphorus-based stabilizer described above, any of 1-hydroxyethylidene-1,1-diphosphonic acid (HEDP) or a salt thereof, and diethylenetriamine penta(methylene phosphonic acid) (DTPP) or a salt thereof; and
  as a carboxylic acid-based stabilizer as described above, any of ethylenediaminetetraacetic acid (EDTA) or a salt thereof, and diethylenetriamine pentaacetic acid (DTPA) or a salt thereof.

In one embodiment of the present invention, the composition for sterilization and cleaning may comprise:
  as a phosphorus-based stabilizer described above, 1-hydroxyethylidene-1,1-diphosphonic acid (HEDP) or a salt thereof; and
  as a carboxylic acid-based stabilizer as described above, ethylenediaminetetraacetic acid (EDTA) or a salt thereof.

In one embodiment of the present invention, the composition for sterilization and cleaning may comprise the phosphorus-based stabilizer in a concentration of 0.0001% by mass or more and less than 0.5% by mass, and the carboxylic acid-based stabilizer in a concentration of 0.0001% by mass or more and less than 0.5% by mass.

In one embodiment of the present invention, the composition for sterilization and cleaning may comprise the phosphorus-based stabilizer in a concentration of 0.0001% to 0.30% by mass, and the carboxylic acid-based stabilizer in a concentration of 0.0001% to 0.30% by mass.

In one embodiment of the present invention, the composition for sterilization and cleaning may comprise the phosphorus-based stabilizer in a concentration of 0.0001% to 0.20% by mass, and the carboxylic acid-based stabilizer in a concentration of 0.0001% to 0.20% by mass.

In one embodiment of the present invention, the composition for sterilization and cleaning may comprise the phosphorus-based stabilizer in a concentration of 0.0001% to 0.10% by mass, and the carboxylic acid-based stabilizer in a concentration of 0.0001% to 0.10% by mass.

(1-2) Sodium Stannate

The composition for sterilization and cleaning of the present invention comprises peracetic acid, hydrogen peroxide, acetic acid and/or a salt thereof, and water, and may also comprise sodium stannate as an additive. By addition of the sodium stannate, the stability of the hydrogen peroxide is improved, and the pH value of the composition for sterilization and cleaning can be adjusted to pH 4.0 to 10.0. The composition for sterilization and cleaning of the present invention may comprise only sodium stannate as an additive, or may comprise sodium stannate in combination with a phosphorus-based stabilizer and/or a carboxylic acid-based stabilizer.

In the composition for sterilization and cleaning of the present invention, the concentration of the sodium stannate may be 0.0001% to 5% by mass, preferably 0.0001% to 1% by mass, more preferably 0.0001% to 0.5% by mass, and further preferably 0.0001% to 0.2% by mass.

(1-3) Phosphate, Citrate, and Tris Base

The composition for sterilization and cleaning of the present invention comprises peracetic acid, hydrogen peroxide, acetic acid and/or a salt thereof, and water, and may further comprise, as an additive(s), one or more selected from a phosphate, a citrate, and a tris base. By addition of one or more selected from a phosphate, a citrate, and a tris base, a change in the pH value after dilution can be further reduced.

Examples of the phosphate that can be used in the composition for sterilization and cleaning of the present invention may include a sodium salt of phosphoric acid and a potassium salt of phosphoric acid, but the examples are not limited thereto. Examples of such a sodium salt of phosphoric acid may include sodium dihydrogen phosphate, disodium hydrogen phosphate, and trisodium phosphate, but the examples are not limited thereto. Examples of such a potassium salt of phosphoric acid may include potassium dihydrogen phosphate, dipotassium hydrogen phosphate, and tripotassium phosphate, but the examples are not limited thereto.

The tris base that can be used in the composition for sterilization and cleaning of the present invention means tris(hydroxymethyl)aminomethane.

(2) Other Components

Hydrogen Peroxide

In the composition for sterilization and cleaning of the present invention, hydrogen peroxide is comprised. In the composition for sterilization and cleaning of the present invention, since hydrogen peroxide itself has sterilizing and/or cleaning ability, the hydrogen peroxide does not only contribute to the enhancement of the sterilizing and/or cleaning effects of the composition as a whole, but also contributes to generation and maintenance of a sufficient amount of peracetic acid as a result of an equilibrium reaction with acetic acid (stability in an aqueous solution). Accordingly, by the combination of acetic acid with hydrogen peroxide, the sterilizing and/or cleaning effects of the composition of the present invention can be further enhanced.

The concentration of the hydrogen peroxide in the composition for sterilization and cleaning of the present invention may be 0.001% to 25% by mass, preferably 0.005% to 20% by mass, more preferably 0.01% to 15% by mass, and further preferably 0.02% to 10% by mass. If the concentration of the hydrogen peroxide is too low, the amount of peracetic acid generated as a result of an equilibrium reaction with acetic acid is not sufficient, and the sterilizing and/or cleaning effects of the present invention are not sufficiently exhibited in some cases. On the other hand, even if the concentration of the hydrogen peroxide is too high, the above-described effects are not increased, and rather, it causes problem in terms of safety in some cases.

Ultrapure hydrogen peroxide can be used as a hydrogen peroxide used in the composition for sterilization and cleaning of the present invention. Impurities comprised in the ultrapure hydrogen peroxide may include aluminum (10 ppt or less), iron (10 ppt or less), and sodium (5 ppt or less). Thus, since the ultrapure hydrogen peroxide comprises such small quantities of impurities, it can improve the stability of the obtained composition for sterilization and cleaning.

Acetic Acid and/or Salt Thereof

The acetic acid used in the composition for sterilization and cleaning of the present invention may be those commonly used in the present technical field. The salt of the acetic acid is not particularly limited, as long as it is an acetate that is alkaline when it is processed into an aqueous solution. Examples of the acetate may include sodium acetate, potassium acetate, lithium acetate, beryllium acetate, magnesium acetate, aluminum acetate, calcium acetate, rubidium acetate, strontium acetate, cesium acetate, barium acetate, and ammonium acetate.

The concentration of the acetic acid and/or a salt thereof in the composition for sterilization and cleaning of the present invention may be 0.01% to 70% by mass, preferably 0.05% to 60% by mass, more preferably 0.1% to 55% by mass, and further preferably 0.2% to 50% by mass.

The concentration of the acetic acid and/or a salt thereof in the composition for sterilization and cleaning of the present invention may be 3.5 to 250 times the concentration of the peracetic acid. In one embodiment of the present invention, the concentration of the acetic acid and/or a salt thereof may be 3.5 to 250 times, 3.5 to 150 times, 3.5 to 100 times, 5 to 250 times, 5 to 150 times, 5 to 100 times, 10 to 250 times, 10 to 150 times, 10 to 100 times, or the like the concentration of the peracetic acid. In a preferred embodiment of the present invention, the concentration of the acetic acid and/or a salt thereof may be 10 to 250 times, 10 to 150 times, or 10 to 100 times the concentration of the peracetic acid. When the concentration of the acetic acid and/or a salt thereof is the above-described concentration, the calcium scale of calcium carbonate, etc adhering to a target for sterilization and cleaning can be sufficiently reduced.

Ultrapure acetic acid can be used as an acetic acid used in the composition for sterilization and cleaning of the present invention. Impurities comprised in the ultrapure acetic acid may include aluminum (10 ppt or less), iron (10 ppt or less), and sodium (10 ppt or less). Thus, since the ultrapure acetic acid comprises such small quantities of impurities, it can improve the stability of the obtained composition for sterilization and cleaning.

Peracetic Acid

The peracetic acid used in the composition for sterilization and cleaning of the present invention may be those commonly used in the present technical field.

The concentration of the peracetic acid in the composition for sterilization and cleaning of the present invention may be 0.001% to 15% by mass. In one embodiment of the present invention, the concentration of the peracetic acid in the composition for sterilization and cleaning may be, for example, 0.001% by mass, 0.005% by mass, 0.01% by mass, 0.1% by mass, 0.3% by mass, 0.4% by mass, 0.5% by mass, 0.6% by mass, 1.0% by mass, 3.0% by mass, 4.0% by mass, 5.0% by mass, 10% by mass, or 15% by mass, but is not limited thereto. In one embodiment of the present invention, the concentration of the peracetic acid in the composition for sterilization and cleaning may be, for example, 0.001% to 15% by mass, 0.001% to 10% by mass, 0.001% to 5% by mass, 0.001% to 3% by mass, 0.005% to 15% by mass, 0.005% to 10% by mass, 0.005% to 5% by mass, 0.005% to 3% by mass, 0.01% to 15% by mass, 0.01% to 10% by mass, 0.01% to 5% by mass, 0.01% to 3% by mass, 0.1% to 15% by mass, 0.1% to 10% by mass, 0.1% to 5% by mass, 0.1% to 3% by mass, 0.3% to 15% by mass, 0.3% to 10% by mass, 0.3% to 5% by mass, 0.3% to 3% by mass, 0.4% to 15% by mass, 0.4% to 10% by mass, 0.4% to 5% by mass, 0.4% to 3% by mass, 0.5% to 15% by mass, 0.5% to 10% by mass, 0.5% to 5% by mass, 0.5% to 3% by mass, 0.6% to 15% by mass, 0.6% to 10% by mass, 0.6% to 5% by mass, 0.6% to 3% by mass, 1.0% to 15% by mass, 1.0% to 10% by mass, 1.0% to 5% by mass, 1.0% to 3% by mass, or the like. In one embodiment of the present invention, the concentration of the peracetic acid in the composition for sterilization and cleaning may be preferably 0.001% to 10% by mass, more preferably 0.005% to 5% by mass, and further preferably 0.01% to 3% by mass.

Other Components

The composition for sterilization and cleaning of the present invention may further comprise, as necessary, additives used in common drugs for sterilization and cleaning, etc., such as, for example, surfactants, thickeners, flavors, coloring agents, and hydrolases, as appropriate. In the composition for sterilization and cleaning of the present invention, the balance other than the hydrogen peroxide, the acetic acid and/or a salt thereof, the peracetic acid, and the additives added as necessary, such as stabilizers, is mainly water.

The composition for sterilization and cleaning of the present invention may be directly used without being diluted, or it may be diluted to any given concentration and may be used as a diluted composition for sterilization and cleaning. As a diluent, water is generally used. Such water used as a diluent may be, for example, pure water, ultrapure water, distilled water, purified water, water for injection, and tap water. The dilution magnification is not particularly limited, as long as it may be a dilution magnification capable of preparing a concentration that exhibits the sterilizing and cleaning effects of a diluted composition for sterilization and cleaning. The dilution magnification is preferably 1 to 10000 times, and more preferably 1 to 1000 times.

C-2. Diluted Composition for Sterilization and Cleaning

The diluted composition for sterilization and cleaning of the present invention comprises peracetic acid, acetic acid and/or a salt thereof, hydrogen peroxide, water, a phosphorus-based stabilizer and/or a carboxylic acid-based stabilizer as an additive(s), and further, additional water used as a diluent. Individual components are as mentioned above.

The diluted composition for sterilization and cleaning of the present invention may be prepared by diluting the above-described composition for sterilization and cleaning with water. As described above, the dilution magnification is not particularly limited, as long as it may be a dilution magnification capable of preparing a concentration that exhibits the sterilizing and cleaning effects of a diluted composition for sterilization and cleaning. The dilution magnification is preferably 1 to 10000 times, and more preferably 1 to 1000 times.

In one embodiment of the present invention, the concentration of the peracetic acid in the diluted composition for sterilization and cleaning may be 0.001% to 1.5% by mass, preferably 0.001% to 1.0% by mass, more preferably 0.005% to 0.5% by mass, and further preferably 0.01% to 0.3% by mass.

In one embodiment of the present invention, the concentration of the acetic acid and/or a salt thereof in the diluted composition for sterilization and cleaning may be 0.01% to 7% by mass, preferably 0.05% to 6% by mass, more preferably 0.1% to 5.5% by mass, and further preferably 0.2% to 5% by mass.

In one embodiment of the present invention, the concentration of the hydrogen peroxide in the diluted composition for sterilization and cleaning may be 0.001% to 2.5% by mass, preferably 0.005% to 2% by mass, more preferably 0.01% to 1.5% by mass, and further preferably 0.02% to 1.0% by mass.

In one embodiment of the present invention, the diluted composition for sterilization and cleaning comprises 0.001% to 1.5% by mass of peracetic acid, 0.01% to 7% by mass of acetic acid and/or a salt thereof, 0.001% to 2.5% by mass of hydrogen peroxide, and water, and also comprises
   a phosphorus-based stabilizer and/or a carboxylic acid-based stabilizer as an additive(s), wherein
      the pH value of the composition may be pH 4.0 to 10.0.

In one embodiment of the present invention, the concentration of the phosphorus-based stabilizer in the diluted composition for sterilization and cleaning may be 0.0001% to 0.05% by mass, preferably 0.0001% to 0.03% by mass, more preferably 0.0001% to 0.02% by mass, and further preferably 0.0001% to 0.01% by mass.

In one embodiment of the present invention, the concentration of the carboxylic acid-based stabilizer in the diluted composition for sterilization and cleaning may be 0.0001% to 0.05% by mass, preferably 0.0001% to 0.03% by mass, more preferably 0.0001% to 0.02% by mass, and further preferably 0.0001% to 0.01% by mass.

In another embodiment of the present invention, the diluted composition for sterilization and cleaning comprises 0.001% to 1.5% by mass of peracetic acid, 0.01% to 7% by mass of acetic acid and/or a salt thereof, 0.001% to 2.5% by mass of hydrogen peroxide, and water, and also comprises
   sodium stannate as an additive, wherein
      the pH value of the composition may be pH 4.0 to 10.0.

In one embodiment of the present invention, the concentration of the sodium stannate in the diluted composition for sterilization and cleaning may be 0.0001% to 0.5% by mass, preferably 0.0001% to 0.1% by mass, more preferably 0.0001% to 0.05% by mass, and further preferably 0.0001% to 0.02% by mass.

C-3. Methods for Producing a Composition for Sterilization and Cleaning and a Diluted Composition for Sterilization and Cleaning In one embodiment of the present invention, a method for producing a composition for sterilization and cleaning may comprise a mixing step of mixing at least the following components:
   (i) an additive;
   (ii) a hydrogen peroxide solution and acetic acid; and
   (iii) acetate.

In this production method, a heat of neutralization is not generated, and good workability is obtained. When the aqueous solution has reached an equilibrium state, peracetic acid appears to be also present in the aqueous solution. However, in the mixing step, peracetic acid may also be added. Individual components are as mentioned above. The order of mixing individual components may be arbitrary, and in the composition for sterilization and cleaning of the present invention, the mixed individual components are in an equilibrium state.

The above-described acetate may be an acetate that is alkaline when it is processed into an aqueous solution. Examples of the acetate that can be used herein may include sodium acetate, potassium acetate, lithium acetate, beryllium acetate, magnesium acetate, aluminum acetate, calcium acetate, rubidium acetate, strontium acetate, cesium acetate, barium acetate, and ammonium acetate, but the examples are not limited thereto. In one embodiment of the present invention, the acetate may be sodium acetate. In another embodiment of the present invention, the acetate may be potassium acetate.

In one embodiment of the present invention, a method for producing a composition for sterilization and cleaning may comprise a mixing step of mixing at least the following components:
   (i) an additive;
   (ii) a hydrogen peroxide solution and acetic acid; and
   (iii) alkali.

In this production method, a heat of neutralization is generated, and a transition speed increases, so that the reaction may be accelerated. When the aqueous solution has reached an equilibrium state, peracetic acid appears to be also present in the aqueous solution. However, in the mixing step, peracetic acid may also be added. Individual components are as mentioned above. The order of mixing individual components may be arbitrary, and in the composition for sterilization and cleaning of the present invention, the mixed individual components are in an equilibrium state.

Examples of the above-described alkali that can be used herein may include sodium hydroxide, potassium hydroxide, lithium hydroxide, beryllium hydroxide, magnesium hydroxide, aluminum hydroxide, calcium hydroxide, rubidium hydroxide, strontium hydroxide, cesium hydroxide, barium hydroxide, and ammonia, but the examples are not limited thereto. In one embodiment of the present invention, the alkali may be sodium hydroxide. In another embodiment of the present invention, the alkali may be potassium hydroxide.

The above-described production method using an alkali may comprise, after completion of the mixing of an additive, acetic acid, and an alkali, a step of mixing a hydrogen peroxide solution with the mixture at 30° C. to 50° C. In this production method, a heat of neutralization is generated. Thus, by utilizing such a heat of neutralization generated as a result of the mixing of an additive, acetic acid, and an alkali, a hydrogen peroxide solution can be mixed with the mixture at 30° C. to 50° C., and a transition speed thereby increases, so that the reaction can be accelerated.

In one embodiment of the present invention, a method for producing a composition for sterilization and cleaning may comprise a mixing step of mixing at least the following components:
   (i) an additive;
   (ii) a hydrogen peroxide solution and acetic acid; and
   (iii) one or more selected from a phosphate, a citrate, and a tris base.

In this production method, when a phosphate or a citrate is used as a component (iii), a heat of neutralization is not generated, and good workability is obtained. On the other hand, in this production method, when a tris base is used as a component (iii), a heat of neutralization is generated, and a transition speed increases, so that the reaction may be accelerated. When the aqueous solution has reached an equilibrium state, peracetic acid appears to be also present in the aqueous solution. However, in the mixing step, peracetic acid may also be added. Individual components are as mentioned above. The order of mixing individual components may be arbitrary, and in the composition for sterilization and cleaning of the present invention, the mixed individual components are in an equilibrium state.

When the tris base is used as a component (iii), the above-described production method may comprise, after completion of the mixing of an additive, acetic acid, and a tris base, a step of mixing a hydrogen peroxide solution with the mixture at 30° C. to 50° C. In this production method, a heat of neutralization is generated. Thus, by utilizing such a heat of neutralization generated as a result of the mixing of an additive, acetic acid, and a tris base, a hydrogen peroxide solution can be mixed with the mixture at 30° C. to 50° C., and a transition speed thereby increases, so that the reaction can be accelerated.

In one embodiment of the present invention, a method for producing a composition for sterilization and cleaning may comprise the following steps (A) and (B):
  a step (A) of mixing, at least, (i) an additive, (ii) a hydrogen peroxide solution and acetic acid, and (iii) acetate, or alkali, or one or more selected from a phosphate, a citrate, and a tris base; and
  a step (B) of leaving an aqueous solution (a) obtained in the step (A) at rest for 1 day or more.

The aqueous solution (a) obtained in the step (A) is left at rest in the step (B), so that the aqueous solution reaches an equilibrium state. In an embodiment of using an acetate, the temperature, at which the aqueous solution is left at rest in the step (B), is preferably 20° C. to 60° C., and more preferably 20° C. to 50° C. In addition, the time, in which the aqueous solution is left at rest in the step (B), is preferably 1 day or more, and it may be, for example, 2 days or more, 3 days or more, 5 days or more, 10 days or more, 30 days or more, etc. In an embodiment of using an alkali or a tris base, as described above, the reaction can be accelerated as a result of generation of a heat of neutralization.

In a further embodiment of the present invention, a method for producing a composition for sterilization and cleaning may comprise the following steps (C) to (E):
  a step (C) of mixing, at least, (ii) a hydrogen peroxide solution and acetic acid and (i) an additive;
  a step (D) of leaving an aqueous solution (c) obtained in the step (C) at rest for 1 day or more; and
  a step (E) of mixing an aqueous solution (d) obtained in the step (D), (iii) acetate, or alkali, or one or more selected from a phosphate, a citrate, and a tris base, and water.

By leaving the aqueous solution (c) obtained in the step (C) at rest, the aqueous solution reaches an equilibrium state. The temperature, at which the aqueous solution is left at rest in the step (D), is preferably 20° C. to 60° C., and more preferably 20° C. to 50° C. In addition, the time, in which the aqueous solution is left at rest in the step (D), is preferably 1 day or more, and it may be, for example, 2 days or more, 3 days or more, 5 days or more, 10 days or more, 30 days or more, etc. Thereafter, acetate, or alkali, or one or more selected from a phosphate, a citrate, and a tris base, and water are mixed with the aqueous solution (d) that has reached an equilibrium state.

The method for producing a composition for sterilization and cleaning of the present invention may further comprise, in the above-described mixing step, adding a metal selected from the group consisting of Al, Zr, and Nb to the mixture. In the above-described mixing step, by adding the aforementioned metal to the mixture, the stability of the mixture can be improved upon the mixing of raw materials (upon formulating). The metal added to the composition for sterilization and cleaning of the present invention may be added, for example, in the form of a standard stock solution of metal. In a preferred embodiment, the standard stock solution of metal may be a standard stock solution having a concentration of 1,000 ppm. The concentration of the metal added to the composition for sterilization and cleaning of the present invention may be in the range of 1000 ppb or less, and may be, for example, 500 ppb or less, 1 ppb to 200 ppb, 10 ppb to 150 ppb, or 50 to 100 ppb. In a preferred embodiment, the metal added in the above-described mixing step is Al.

In one embodiment of the present invention, the method for producing a diluted composition for sterilization and cleaning may comprise,
  a mixing step of mixing at least the following components:
    (i) an additive;
    (ii) a hydrogen peroxide solution and acetic acid; and
    (iii) acetate, or alkali, or one or more selected from a phosphate, a citrate, and a tris base, and
  a dilution step of diluting the obtained mixed solution.

When the aqueous solution has reached an equilibrium state, peracetic acid appears to be also present in the aqueous solution. However, in the mixing step, peracetic acid may also be added. Individual components are as mentioned above. In the method for producing a diluted composition for sterilization and cleaning of the present invention, the dilution step may comprise mixing the mixture obtained in the mixing step with water. The water used as a diluent may be, for example, pure water, ultrapure water, distilled water, purified water, water for injection, or tap water.

Sterilization and Cleaning Method Using a Composition for Sterilization and Cleaning The above-described composition for sterilization and cleaning or the above-described diluted composition for sterilization and cleaning of the present invention can each be used in the sterilization, cleaning and the like of, for example, medical devices, containers for beverages and foods, industrial drainages, cooling water for air conditioning facilities, clothes, cookware, tableware, bathroom, kitchen, washing machine tub, bath kettle, furniture, and companion animals.

In one embodiment of the present invention, a method for sterilizing and cleaning a medical device, in which the above-described composition for sterilization and cleaning or the above-described diluted composition for sterilization and cleaning is used, is provided. In the sterilization and cleaning method of the present invention, the above-described method for sterilizing and cleaning a medical device may be any of an immersion method, a spray method, and a coating method. In the method for sterilizing and cleaning a medical device of the present invention, the used amount of the composition for sterilization and cleaning or the diluted composition for sterilization and cleaning, or the time required for sterilization and cleaning, may be selected, as appropriate, depending on the type or amount of microorganisms, the concentration of the composition for sterilization and cleaning or the diluted composition for sterilization and cleaning, etc.

In the sterilization and cleaning method of the present invention, examples of the above-described medical device may include dialyzers, endoscopic instruments, surgical instruments, obstetric and/or urologic instruments, anesthetic apparatuses, artificial respiration apparatuses, dental instruments, and injection needles, but the examples are not limited thereto. In the sterilization and cleaning method of the present invention, the medical device is preferably a dialyzer.

EXAMPLES

Hereinafter, the examples of the present invention will be described. However, these examples are provided for illustrating the embodiments of the present invention, and thus, are not intended to limit the scope of the present invention.

Embodiment A

Method of Measuring Hydrogen Peroxide Concentration

In the present invention, the concentration of the hydrogen peroxide in the composition for sterilization and cleaning (peracetic acid composition) was measured according to redox titration. Specifically, approximately 0.1 g of a sample was precisely weighed, and was then placed in a 250-mL Erlenmeyer flask. Then, 100 mL of pure water and 10 mL of 1.8 mol/L sulfuric acid were added thereto to prepare a test solution. Several drops of a ferroin indicator solution were added to this test solution, followed by titration with a 0.1 mol/L cerium(IV) sulfate solution, so that the hydrogen peroxide concentration was calculated.

Method for Measuring Acetic Acid and Peracetic Acid Concentrations

In the present invention, the concentrations of the acetic acid and the peracetic acid in the composition for sterilization and cleaning (peracetic acid composition) were measured according to neutralization titration. Specifically, approximately 0.1 g of a sample was precisely weighed, and was then placed in a 100-mL beaker. Then, approximately 50 mL of pure water was added thereto to prepare a test solution. This test solution was titrated with a 0.1 mol/L sodium hydroxide solution. Based on the additive amount at a first inflection point, the acetic acid concentration was calculated. Based on the additive amount from a first inflection point to a second inflection point, the peracetic acid concentration was calculated.

<Stability Test>

In the present invention, the total concentration of peroxide in the composition for sterilization and cleaning (peracetic acid composition) was measured according to an iodometric method. Specifically, approximately 0.1 g of a sample was precisely weighed, and was then placed in a 250-mL Erlenmeyer flask. Then, 100 mL of pure water and 10 mL of 1.8 mol/L sulfuric acid were added thereto, and thereafter, 10 mL of a solution containing 10% by mass of potassium iodide and several drops of a solution containing 1% by mass of ammonium molybdate were added to the mixture to prepare a test solution. A 0.1 mol/L sodium thiosulfate solution was added dropwise to this test solution. Using starch as an indicator agent, a point at which a bluish-purple color disappeared from the solution and the solution became colorless was determined as an end point, and free iodine was quantified. Based on the amount of the iodine, the total peroxide concentration was calculated, in terms of hydrogen peroxide.

The total peroxide (TPO) concentration at the time of the addition was set at 100, and the stability of the composition for sterilization and cleaning (peracetic acid composition) was then calculated based on the ratio of the total peroxide concentration upon the measurement. The stability of the composition was evaluated as follows:

A: 93% or more (good);
B: 90% or more and less than 93% (practical); and
C: less than 90% (impractical).

Preparation of a Spore Suspension

A *Bacillus cereus* standard strain (manufactured by Microbiologics, product name: *Bacillus cereus* ATCC10876) was coated onto an NGKG agar medium (manufactured by AZONE, product name: SANI-SPEC raw medium), and was then cultured at 35° C. for 7 days. Thereafter, sterile distilled water was added to the resulting agar medium, and a cell mass was then collected by scraping with a cell spreader. Thereafter, the cell mass was washing with sterile distilled water through centrifugation. In order to obtain only the spores, the resultant was heated at 80° C. for 10 minutes, and the surviving cells were prepared as a spore suspension.

Sterilization Test

The composition for sterilization and cleaning of the present invention (peracetic acid composition) was 40 to 300 times diluted with sterile distilled water to prepare a sample solution, in which the peracetic acid concentration became 90 to 200 ppm. Thereafter, 50 μL, of the spore suspension was added to 5 mL of each sample solution, so that the sample solution was allowed to act on the spore suspension at 25° C. for 120 minutes. After completion of the action, the resulting solution was 10 times diluted with a 0.1 mol/L sterile sodium thiosulfate solution, and the diluted solution was then cultured at 35° C. for 48 hours, using a *Bacillus cereus* detection medium (manufactured by NIS SUI PHARMACEUTICAL CO., LTD., product name: Compact Dry X-BC). Thereafter, the number of living cells was measured. On the other hand, the number of living cells in the spore suspension was measured, and it was defined to be the number of living cells at the starting time of the test.

Example A-1

Pure water (21.0 g), 0.02 g of 60% by mass of 1-hydroxyethylidene-1,1-diphosphonic acid (HEDP, manufactured by Italmatch Japan, product name: D-Quest 2010), 0.01 g of ethylenediaminetetraacetic acid disodium dihydrate ($EDTA \cdot 2Na \cdot 2H_2O$, manufactured by MP Biomedicals, Inc.), 55.8 g of sodium acetate trihydrate (manufactured by FUJIFILM Wako Pure Chemical Corporation), 9.0 g of glacial acetic acid (manufactured by Showa Denko K. K., product name: 99% Pure and Good Acetic Acid), 14.2 g of 45% by mass of hydrogen peroxide (manufactured by Mitsubishi Gas Chemical Company, Inc., product name: SER45), and 0.01 g of polyoxyethylene (4.5) lauryl ether acetic acid (Kao Corporation, product name: KAO AKYPO RLM-45), were mixed in a PE container. The total peroxide concentration was found to be 6.1% at the time of the formulation. After completion of the mixing, the mixture was matured at 25° C. for 7 days, so as to obtain a composition for sterilization and cleaning (peracetic acid composition), comprising 5.8% by mass of hydrogen peroxide, 8.6% by mass of acetic acid, 0.45% by mass of peracetic acid, 33.6% by mass of sodium acetate, 0.01% by mass of 1-hydroxyethylidene-1,1-diphosphonic acid, 0.01% by mass of ethylenediaminetetraacetic acid disodium, and 0.01% by mass of polyoxyethylene (4.5) lauryl ether acetic acid, and having a pH of 5.1. A stability test and a sterilization test were performed on the obtained composition for sterilization and cleaning (peracetic acid composition). The results are shown in Table A-1 and Table A-2 (shown in [Table 1] and [Table 2]).

Examples A-2 to A-4 and Reference Example A-1

Compositions for sterilization and cleaning were produced in the same manner as that of Example A-1, with the exception that the formulation as shown in Table A-1 was applied. A stability test and a sterilization test were performed on the obtained compositions for sterilization and cleaning (peracetic acid compositions). The results are shown in Table A-1 and Table A-2.

Comparative Example A-1

Pure water (37.1 g), 0.2 g of pyrophosphoric acid (manufactured by JUNSEI CHEMICAL CO., LTD.; product name: Diphosphoric Acid), 37.5 g of glacial acetic acid (manufactured by Showa Denko K. K., product name: 99% Pure and Good Acetic Acid), and 14.2 g of 45% by mass of hydrogen peroxide (manufactured by Mitsubishi Gas Chemical Company, Inc., product name: SER45) were mixed in a PE container. The total peroxide concentration was found to be 6.1% at the time of the formulation. After completion of the mixing, the mixture was matured at 50° C. for 2 days and then, at 25° C. for 2 days, so as to obtain a composition for sterilization and cleaning (peracetic acid composition), comprising 7.5% by mass of hydrogen peroxide, 32.4% by mass of acetic acid, 6.0% by mass of peracetic acid, and 0.2% by mass of pyrophosphoric acid, and having a pH of 1.1. A stability test and a sterilization test were performed on the obtained composition for sterilization and cleaning (peracetic acid composition). The results are shown in Table A-1 and Table A-2.

As described above, according to the present invention, a composition for sterilization and cleaning of medical devices, which has high stability of peroxide and a drainage of which satisfies the sewage discharge standards, can be provided.

TABLE A-1

[Table 1]

| | Formulation | | | | | | | | |
|---|---|---|---|---|---|---|---|---|---|
| No. | Water [g] | 99 mass % glacial acetic acid [g] | 45 mass % hydrogen peroxide solution [g] | Sodium acetate trihydrate [g] | 60 mass % HEDP [g] | Pyrophosphoric acid [g] | EDTA•2Na•2H$_2$O [g] | Polyoxyethylene (4.5) lauryl ether acetic acid [g] | TPO concentration upon formulation [wt %] |
| Ex. A-1 | 21.0 | 9.0 | 14.2 | 55.8 | 0.02 | 0.00 | 0.01 | 0.01 | 6.1 |
| Ex. A-2 | 20.9 | 9.0 | 14.2 | 55.8 | 0.02 | 0.00 | 0.01 | 0.11 | 6.1 |
| Ex. A-3 | 13.7 | 10.0 | 14.2 | 62.0 | 0.02 | 0.00 | 0.01 | 0.05 | 6.1 |
| Ex. A-4 | 13.7 | 10.0 | 14.2 | 62.0 | 0.02 | 0.00 | 0.01 | 0.11 | 6.1 |
| Comp. Ex. A-1 | 37.1 | 37.5 | 25.2 | 0.0 | 0.00 | 0.20 | 0.00 | 0.00 | 11.5 |
| Ref. Ex. A-1 | 21.0 | 9.0 | 14.2 | 55.8 | 0.02 | 0.00 | 0.01 | 0.00 | 6.1 |

| | Maturation at 25° C. for 7 days after formulation | | | | | | | | | |
|---|---|---|---|---|---|---|---|---|---|---|
| | | | | | Phosphorus | | Carboxylic | Polyoxyethylene (4.5) lauryl | | |
| No. | Peractic acid [wt %] | Hydrogen peroxide [wt %] | Acetic acid [wt %] | Na acetate [wt %] | HEDP [wt %] | Pyrophosphoric acid [wt %] | acid EDTA•2Na [wt %] | ether acetic acid [wt %] | pH | pH after 50-fold dilution | Stability |
| Ex. A-1 | 0.45 | 5.8 | 8.6 | 33.6 | 0.01 | 0.00 | 0.01 | 0.01 | 5.7 | 5.1 | A |
| Ex. A-2 | 0.44 | 5.8 | 8.6 | 33.6 | 0.01 | 0.00 | 0.01 | 0.10 | 5.7 | 5.1 | A |
| Ex. A-3 | 0.47 | 5.7 | 9.5 | 37.4 | 0.01 | 0.00 | 0.01 | 0.05 | 5.8 | 5.1 | A |
| Ex. A-4 | 0.46 | 5.8 | 9.6 | 37.4 | 0.01 | 0.00 | 0.01 | 0.10 | 5.8 | 5.1 | A |
| Comp. Ex. A-1 | 6.0 | 7.5 | 32.4 | 0.0 | 0.00 | 0.20 | 0.00 | 0.00 | 1.1 | 3.2 | A |
| Ref. Ex. A-1 | 0.5 | 5.8 | 8.6 | 33.6 | 0.01 | 0.00 | 0.01 | 0.00 | 5.7 | 5.1 | A |

TABLE A-2

[Table 2]

| No. | Dilution magnification [-fold] | Peractic acid [ppm] | Hydrogen peroxide [ppm] | Acetic acid [ppm] | HEDP [ppm] | Pyrophosphoric acid [ppm] | EDTA·2Na [ppm] | Polyoxyethylene (4.5) lauryl ether acetic acid [ppm] | Sterilization test (Bacillus cereus) [CFU/mL] At start | After 120 min |
|---|---|---|---|---|---|---|---|---|---|---|
| Ex. A-1 | 40 | 120 | 1500 | 2200 | 2.5 | 0.0 | 2.5 | 2.5 | $4.8 \times 10^5$ | $2.9 \times 10^3$ |
| Ex. A-2 | 50 | 90 | 1200 | 1700 | 2.0 | 0.0 | 2.0 | 20 | $4.8 \times 10^5$ | $4.4 \times 10^3$ |
| Ex. A-3 | 40 | 120 | 1400 | 2400 | 2.5 | 0.0 | 2.5 | 13 | $4.8 \times 10^5$ | 500 |
| Ex. A-4 | 40 | 120 | 1400 | 2400 | 2.5 | 0.0 | 2.5 | 25 | $4.8 \times 10^5$ | Less than 100 |
| Comp. Ex. A-1 | 300 | 200 | 270 | 1100 | 0.0 | 7.0 | 0.0 | 0 | $4.8 \times 10^5$ | $7.1 \times 10^4$ |
| Ref. Ex. A-1 | 50 | 90 | 1200 | 1700 | 2.0 | 0.0 | 2.0 | 0 | $4.8 \times 10^5$ | $8.4 \times 10^4$ |

Embodiment B

Method of Measuring Hydrogen Peroxide Concentration in a Composition for Sterilization and Cleaning In the present invention, the concentration of the hydrogen peroxide in the composition for sterilization and cleaning (peracetic acid composition) was measured according to redox titration. Specifically, approximately 0.1 g of a sample of the composition for sterilization and cleaning was precisely weighed, and was then placed in a 250-mL Erlenmeyer flask. Then, 10 mL of 20% by mass of sulfuric acid was added thereto to prepare a test solution. Several drops of a ferroin indicator solution were added to this test solution, followed by titration with a 0.1 mol/L cerium(IV) sulfate solution, so that the hydrogen peroxide concentration was calculated.

Method for Measuring Acetic Acid and Peracetic Acid Concentrations in a Composition for Sterilization and Cleaning In the present invention, the concentrations of the acetic acid and the peracetic acid in the composition for sterilization and cleaning (peracetic acid composition) were measured according to neutralization titration. Specifically, approximately 0.1 g of a sample of the composition for sterilization and cleaning was precisely weighed, and was then placed in a 100-mL beaker. Then, approximately 50 mL of pure water was added thereto to prepare a test solution. This test solution was titrated with a 0.1 mol/L sodium hydroxide solution. Based on the additive amount at a first inflection point, the acetic acid concentration was calculated. Based on the additive amount from a first inflection point to a second inflection point, the peracetic acid concentration was calculated.

Stability Test of a Composition for Sterilization and Cleaning

In the present invention, the total concentration of peroxide in the composition for sterilization and cleaning (peracetic acid composition) was measured according to an iodometric method. Specifically, approximately 0.1 g of a sample of the composition for sterilization and cleaning was precisely weighed, and was then placed in a 250-mL Erlenmeyer flask. Then, 100 mL of pure water and 10 mL of 20% by mass of sulfuric acid were added thereto, and thereafter, 10 mL of a solution containing 10% by mass of potassium iodide and several drops of a solution containing 1% by mass of ammonium molybdate were added to the mixture to prepare a test solution. A 0.1 mol/L sodium thiosulfate solution was added dropwise to this test solution. Using starch as an indicator agent, a point at which a bluish-purple color disappeared from the solution and the solution became colorless was determined as an end point, and free iodine was quantified. Based on the amount of the iodine, the total peroxide concentration was calculated, in terms of hydrogen peroxide.

The total peroxide (TPO) concentration at the time of the addition was set at 100, and the stability of the composition for sterilization and cleaning (peracetic acid composition) of the present invention was then calculated based on the ratio of the total peroxide concentration upon the measurement. The stability of the composition was evaluated as follows:
A: 93% or more (good);
B: 90% or more and less than 93% (practical); and
C: less than 90% (impractical).

Preparation of a Spore Suspension

A *Bacillus cereus* standard strain (manufactured by Microbiologics, product name: *Bacillus cereus* ATCC10876) was coated onto an NGKG agar medium (manufactured by AZONE, product name: SANI-SPEC raw medium), and was then cultured at 35° C. for 7 days. Thereafter, sterile distilled water was added to the resulting agar medium, and a cell mass was then collected by scraping with a cell spreader. Thereafter, the cell mass was washing with sterile distilled water through centrifugation. In order to obtain only the spores, the resultant was heated at 80° C. for 10 minutes, and the surviving cells were prepared as a spore suspension.

Sterilization Test

The composition for sterilization and cleaning of the present invention (peracetic acid composition) was diluted with sterile distilled water to prepare a sample solution, in which the peracetic acid concentration became 1000 ppm. Thereafter, 50 μL of the spore suspension was added to 5 mL of each sample solution, so that the sample solution was allowed to act on the spore suspension at 25° C. for 5 to 30 minutes. After completion of the action, the resulting solution was 10 times diluted with a 0.1 mol/L sterile sodium thiosulfate solution, and the diluted solution was then cultured at 35° C. for 48 hours, using a *Bacillus cereus* detection medium (manufactured by NISSUI PHARMACEUTICAL CO., LTD., product name: Compact Dry X-BC). Thereafter, the number of living cells was measured. On the other hand, the number of living cells in the spore suspension was measured, and it was defined to be the number of living cells at the starting time of the test.

Production of Calcium Carbonate Scale

Calcium chloride (manufactured by FUJIFILM Wako Pure Chemical Corporation) and sodium hydrogen carbonate (manufactured by FUJIFILM Wako Pure Chemical Corporation) were dissolved in pure water to prepare a calcium carbonate aqueous solution (900 mg/L $CaCO_3$). While an SUS316 plate (D 1.0 ×H 40 ×W 40 mm) was heated at 120° C., a total of 20 mL of the calcium carbonate aqueous solution was added dropwise onto the plate, so as to produce a calcium carbonate scale.

Scale Removal Test

The aqueous solution for sterilization and cleaning (peracetic acid composition) of the present invention was diluted with distilled water to prepare a sample solution having a peracetic acid concentration of 200 ppm. The SUS316 plate, to which the calcium carbonate scale adhered, was immersed in 10 mL of each sample solution for 1 hour, and was then washed with 10 mL of pure water, followed by drying it. A change in the weight of the calcium carbonate scale-adhering SUS316 plate before and after the immersion thereof in the sample solution was defined as a scale removal amount. The scale removal amount was expressed as a relative value when the value described in Comparative Example 1 was set at 1. As the numerical value of the scale removal amount increases, the scale removal ability increases.

Adsorption of protein

Bovine serum albumin (manufactured by FUJIFILM Wako Pure Chemical Corporation) was used as a protein. Bovine serum albumin was dissolved in pure water to prepare a solution containing 0.3% by mass of albumin. Approximately 0.5 g of SUS304 balls (manufactured by AZONE) was placed in a sample boat for solid TC measurement, and 1 mL of the albumin solution was then added dropwise thereto. Thereafter, vacuum drying was carried out at 40° C. for 2 hours, so that albumin was adsorbed on the SUS304 balls.

Protein Removal Test

The aqueous solution for sterilization and cleaning (peracetic acid composition) of the present invention was diluted with distilled water to prepare a sample solution having a peracetic acid concentration of 200 ppm. The sample boat for solid TC measurement containing the SUS304 balls, on which albumin was adsorbed, was immersed in 20 mL of each sample solution, and it was then shaken in a water bath at 40° C. for 1 hour. Thereafter, the resultant was washed with 10 mL of pure water, and was vacuum-dried at 40° C. for 2 hours. Thereafter, the total carbon amount was measured using a solid TC measurement device (manufactured by Shimadzu Corporation, product name: TOC-VCSN, SSM-5000A), and the remaining protein amount was then calculated from the carbon amount. The remaining protein amount was expressed as a relative value when the value described in Comparative Example 1 was set at 1. As the numerical value of the remaining protein amount decreases, the protein removal ability increases.

Example B-1

A hydrogen peroxide solution (35% by mass) (manufactured by Mitsubishi Gas Chemical Company, Inc.; 35% hydrogen peroxide), glacial acetic acid (manufactured by Showa Denko K. K., product name: 99% Pure and Good Acetic Acid), pyrophosphoric acid (manufactured by JUNSEI CHEMICAL CO., LTD.; product name: Diphosphoric Acid), pure water, and polyoxyethylene (10) lauryl ether acetic acid (manufactured by Kao Corporation, product name: KAO AKYPO RLM-100) were mixed, so that 11.5% by mass of hydrogen peroxide, 37.5% by mass of acetic acid, 0.2% pyrophosphoric acid, and 1.0% polyoxyethylene (10) lauryl ether acetic acid could be obtained. After completion of the mixing, the obtained mixture was left at rest at 25° C. for 11 days, so as to obtain a composition for sterilization and cleaning, comprising 6.5% by mass of peracetic acid, 8.4% by mass of hydrogen peroxide, 32.5% by mass of acetic acid, 0.2% by mass of pyrophosphoric acid, and 1.0% by mass of polyoxyethylene (10) lauryl ether acetic acid. A sterilization test, a stability test, a scale removal test, and a protein removal test were carried out on the obtained composition for sterilization and cleaning. The results are shown in Table B-1, Table B-3, and Table B-5 (shown in [Table 3], [Table 5], and [Table 7]).

Examples B-2 to B-13 and Comparative Examples B-1 to B-10

The compositions for sterilization and cleaning, each having the concentration shown in Table B-1 and Table B-2 (shown in [Table 3] and [Table 4]), were obtained in the same manner as that of Example B-1. A sterilization test, a stability test, a scale removal test, and a protein removal test were carried out on the obtained compositions for sterilization and cleaning. The results are shown in Table B-1 to Table B-5 (shown in [Table 3] to [Table 7]).

Example B-14

A hydrogen peroxide solution (35% by mass) (manufactured by Mitsubishi Gas Chemical Company, Inc.; 35% hydrogen peroxide), glacial acetic acid (manufactured by Showa Denko K. K., product name: 99% Pure and Good Acetic Acid), pyrophosphoric acid (manufactured by JUNSEI CHEMICAL CO., LTD.; product name: Diphosphoric Acid), pure water, and polyoxyethylene (10) lauryl ether acetic acid (manufactured by Kao Corporation, product name: KAO AKYPO RLM-100) were mixed, so that 15.2% by mass of hydrogen peroxide, 9.3% by mass of acetic acid, 0.05% by mass of pyrophosphoric acid, and 1.0% by mass of polyoxyethylene (10) lauryl ether acetic acid could be obtained. After completion of the mixing, the obtained mixture was left at rest at 25° C. for 11 days, so as to obtain a composition for sterilization and cleaning, comprising 1.6% by mass of peracetic acid, 14.5% by mass of hydrogen peroxide, 8.1% by mass of acetic acid, 0.05% by mass of pyrophosphoric acid, and 1.0% by mass of polyoxyethylene (10) lauryl ether acetic acid. A sterilization test, a stability test, a scale removal test, and a protein removal test were carried out on the obtained composition for sterilization and cleaning. The results are shown in Table B-1 and Table B-3.

Example B-15 and Comparative Example B-11

The compositions for sterilization and cleaning, each having the concentration shown in Table B-1 and Table B-2, were obtained in the same manner as that of Example B-14. A sterilization test and a stability test were carried out on the obtained compositions for sterilization and cleaning. The results are shown in Table B-1 to Table B-4.

Example B-16

A hydrogen peroxide solution (35% by mass) (manufactured by Mitsubishi Gas Chemical Company, Inc.; 35% hydrogen peroxide), glacial acetic acid (manufactured by Showa Denko K. K., product name: 99% Pure and Good Acetic Acid), 1-hydroxyethylidene-1,1-diphosphonic acid (HEDP) (manufactured by Italmatch Japan, product name: D-Quest 2010), pure water, and polyoxyethylene (10) lauryl ether acetic acid (manufactured by Kao Corporation, product name: KAO AKYPO RLM-100) were mixed, so that 12.1% by mass of hydrogen peroxide, 59.1% by mass of acetic acid, 0.7% by mass of 1-hydroxyethylidene-1,l-diphosphonic acid, and 1.0% by mass of polyoxyethylene (10) lauryl ether acetic acid could be obtained. After completion of the mixing, the obtained mixture was left at rest at 25° C. for 11 days, so as to obtain a composition for sterilization and cleaning, comprising 13.7% by mass of peracetic acid, 5.4% by mass of hydrogen peroxide, 48.4% by mass of acetic acid, 0.7% by mass of 1-hydroxyethylidene-1,1-diphosphonic acid, and 1.0% by mass of polyoxyethylene (10) lauryl ether acetic acid. A sterilization test and a stability test were carried out on the obtained composition for sterilization and cleaning. The results are shown in Table B-1 and Table B-3.

Example B-17 and Comparative Example B-12

The compositions for sterilization and cleaning, each having the concentration shown in Table B-1 and Table B-2, were obtained in the same manner as that of Example B-16. A sterilization test and a stability test were carried out on the obtained compositions for sterilization and cleaning. The results are shown in Table B-1 to Table B-4.

Example B-18

A hydrogen peroxide solution (35% by mass) (manufactured by Mitsubishi Gas Chemical Company, Inc.; 35% hydrogen peroxide), glacial acetic acid (manufactured by Showa Denko K. K., product name: 99% Pure and Good Acetic Acid), 1-hydroxyethylidene-1,1-diphosphonic acid (HEDP) (manufactured by Italmatch Japan, product name: D-Quest 2010), pure water, and polyoxyethylene (10) lauryl ether acetic acid (manufactured by Kao Corporation, product name: KAO AKYPO RLM-100) were mixed, so that 20.3% by mass of hydrogen peroxide, 10.2% by mass of acetic acid, 0.1% by mass of 1-hydroxyethylidene-1,1-diphosphonic acid, and 1.0% by mass of polyoxyethylene (10) lauryl ether acetic acid could be obtained. After completion of the mixing, the obtained mixture was left at rest at 25° C. for 11 days, so as to obtain a composition for sterilization and cleaning, comprising 2.4% by mass of peracetic acid, 19.3% by mass of hydrogen peroxide, 8.4% by mass of acetic acid, 0.1% by mass of 1-hydroxyethylidene-1,1-diphosphonic acid, and 1.0% by mass of polyoxyethylene (10) lauryl ether acetic acid. A sterilization test and a stability test were carried out on the obtained composition for sterilization and cleaning. The results are shown in Table B-1 to Table B-4.

Example B-19 and Comparative Example B-13

The compositions for sterilization and cleaning, each having the concentration shown in Table B-1 and Table B-2, were obtained in the same manner as that of Example B-18. A sterilization test and a stability test were carried out on the obtained compositions for sterilization and cleaning. The results are shown in Table B-1 to Table B-4.

TABLE B-1

[Table 3]

| | Peracetic acid concentration [ppm] | Hydrogen peroxide concentration [ppm] | Acetic acid concentration [ppm] | Compounding agent/ concentration [ppm] | |
|---|---|---|---|---|---|
| Example B-1 | 65000 | 84000 | 325000 | Polyoxyethylene (10) lauryl ether acetic acid | 10000 |
| Example B-2 | 65000 | 84000 | 325000 | Polyoxyethylene (10) lauryl ether acetic acid | 5000 |
| Example B-3 | 65000 | 84000 | 325000 | Polyoxyethylene (10) lauryl ether acetic acid | 1000 |
| Example B-4 | 65000 | 84000 | 325000 | Polyoxyethylene (4.5) lauryl ether acetic acid | 10000 |
| Example B-5 | 65000 | 84000 | 325000 | Polyoxyethylene (4.5) laurryl ether acetic acid | 5000 |
| Example B-6 | 65000 | 84000 | 325000 | Polyoxyethylene (4.5) lauryl ether acetic acid | 1000 |
| Example B-7 | 65000 | 84000 | 325000 | Polyoxyethylene (10) lauryl ether acetic acid | 10000 |
| Example B-8 | 65000 | 84000 | 325000 | Polyoxyethylene (10) lauryl ether acetic acid | 10000 |
| Example B-9 | 65000 | 84000 | 325000 | Polyoxyethylene (10) lauryl ether acetic acid | 10000 |
| Example B-10 | 65000 | 84000 | 325000 | Polyoxyethylene (4.5) lauryl ether acetic acid | 10000 |
| Example B-11 | 65000 | 84000 | 325000 | Polyoxyethylene (4.5) lauryl ether acetic acid | 10000 |
| Example B-12 | 65000 | 84000 | 325000 | Polyoxyethylene (4.5) lauryl ether acetic acid | 10000 |
| Example B-13 | 65000 | 84000 | 325000 | Polyoxyethylene (4.5) lauryl ether acetic acid | 10000 |

TABLE B-1-continued

[Table 3]

| | | | | | |
|---|---|---|---|---|---|
| Example B-14 | 16100 | 145100 | 80700 | Polyoxyethylene (10) lauryl ether acetic acid | 10000 |
| Example B-15 | 16100 | 145100 | 80700 | Polyoxyethylene (4.5) lauryl ether acetic acid | 10000 |
| Example B-16 | 137400 | 53500 | 484400 | Polyoxyethylene (10) lauryl ether acetic acid | 10000 |
| Example B-17 | 137400 | 53500 | 484400 | Polyoxyethylene (4.5) lauryl ether acetic acid | 10000 |
| Example B-18 | 23800 | 192600 | 83700 | Polyoxyethylene (10) lauryl ether acetic acid | 10000 |
| Example B-19 | 23800 | 192600 | 83700 | Polyoxyethylene (4.5) lauryl ether acetic acid | 10000 |

| | Stabilizer/ concentration [ppm] | | Chelating agent concentration [ppm] | | Stability |
|---|---|---|---|---|---|
| Example B-1 | Pyrophosphoric acid | 2000 | — | 0 | A |
| Example B-2 | Pyrophosphoric acid | 2000 | — | 0 | A |
| Example B-3 | Pyrophosphoric acid | 2000 | — | 0 | A |
| Example B-4 | Pyrophosphoric acid | 2000 | — | 0 | A |
| Example B-5 | Pyrophosphoric acid | 2000 | — | 0 | A |
| Example B-6 | Pyrophosphoric acid | 2000 | — | 0 | A |
| Example B-7 | Pyrophosphoric acid | 2000 | EDTA•2Na | 5395 | A |
| Example B-8 | Pyrophosphoric acid | 2000 | EDTA•2NH$_4$ | 4810 | A |
| Example B-9 | Pyrophosphoric acid | 2000 | Dipicolinic acid | 2405 | A |
| Example B-10 | Pyrophosphoric acid | 2000 | EDTA•2Na | 5395 | A |
| Example B-11 | Pyrophosphoric acid | 2000 | EDTA•2NH$_4$ | 4810 | A |
| Example B-12 | Pyrophosphoric acid | 2000 | HEDP | 2990 | A |
| Example B-13 | Pyrophosphoric acid | 2000 | Dipicolinic acid | 2405 | A |
| Example B-14 | Pyrophosphoric acid | 500 | — | 0 | A |
| Example B-15 | Pyrophosphoric acid | 500 | — | 0 | A |
| Example B-16 | HEDP | 7000 | — | 0 | A |
| Example B-17 | HEDP | 7000 | — | 0 | A |
| Example B-18 | HEDP | 1200 | — | 0 | A |
| Example B-19 | HEDP | 1200 | — | 0 | A |

TABLE B-2

[Table 4]

| | Peracetic acid concentration [ppm] | Hydrogen peroxide concentration [ppm] | Acetic acid concentration [ppm] | Compounding agent/ concentration [ppm] |
|---|---|---|---|---|
| Comp. Ex. B-1 | 65000 | 84000 | 325000 | Non |
| Comp. Ex. B-2 | 65000 | 84000 | 325000 | Polyoxyethylene octyl ether acetic acid |
| Comp. Ex. B-3 | 65000 | 84000 | 325000 | Polyoxyethylene hexyl/octyl ether acetic acid |
| Comp. Ex. B-4 | 65000 | 84000 | 325000 | Polyoxyethylene oleyl ether acetic acid |
| Comp. Ex. B-5 | 65000 | 84000 | 325000 | Sodium polyoxyethylene lauryl ether sulfate |
| Comp. Ex. B-6 | 65000 | 84000 | 325000 | Sodium dodecyl sulfate |
| Comp. Ex. B-7 | 65000 | 84000 | 325000 | Polyoxyethylene (23) lauryl ether |
| Comp. Ex. B-8 | 65000 | 84000 | 325000 | Polyoxyethylene (20) cetyl ether |
| Comp. Ex. B-9 | 65000 | 84000 | 325000 | Polyoxyethylene (20) sorbitan monolaurate |
| Comp. Ex. B-10 | 65000 | 84000 | 325000 | Polyoxyethylene (8) octyl phenyl ether |
| Comp. Ex. B-11 | 16100 | 145100 | 80700 | — |
| Comp. Ex. B-12 | 137400 | 53500 | 484400 | — |
| Comp. Ex. B-13 | 23800 | 192600 | 83700 | — |

| | Compounding agent/ concentration [ppm] | Stabilizer/ concentration [ppm] | | Chelating agent/ concentration [ppm] | Stability |
|---|---|---|---|---|---|
| Comp. Ex. B-1 | 0 | Pyrophosphoric acid | 2000 | — | 0 | A |
| Comp. Ex. B-2 | 10000 | Pyrophosphoric acid | 2000 | — | 0 | A |
| Comp. Ex. B-3 | 10000 | Pyrophosphoric acid | 2000 | — | 0 | A |
| Comp. Ex. B-4 | 10000 | Pyrophosphoric acid | 2000 | — | 0 | A |
| Comp. Ex. B-5 | 10000 | Pyrophosphoric acid | 2000 | — | 0 | C |

TABLE B-2-continued

[Table 4]

| | | | | | | |
|---|---|---|---|---|---|---|
| Comp. Ex. B-6 | 10000 | Pyrophosphoric acid | 2000 | — | 0 | A |
| Comp. Ex. B-7 | 10000 | Pyrophosphoric acid | 2000 | — | 0 | A |
| Comp. Ex. B-8 | 10000 | Pyrophosphoric acid | 2000 | — | 0 | A |
| Comp. Ex. B-9 | 10000 | Pyrophosphoric acid | 2000 | — | 0 | A |
| Comp. Ex. B-10 | 10000 | Pyrophosphoric acid | 2000 | — | 0 | A |
| Comp. Ex. B-11 | 0 | Pyrophosphoric acid | 500 | — | 0 | A |
| Comp. Ex. B-12 | 0 | HEDP | 7000 | — | 0 | A |
| Comp. Ex. B-13 | 0 | HEDP | 1200 | — | 0 | A |

TABLE B-3

[Table 5]

| | Peracetic acid concentration [ppm] upon sterilization test | Hydrogen peroxide concentration [ppm] upon sterilization test | Acetic acid concentration [ppm] | Compounding agent/ concentration [ppm] upon sterilization test | |
|---|---|---|---|---|---|
| Example B-1 | 1000 | 1292 | 5000 | Polyoxyethylene (10) lauryl ether acetic acid | 154 |
| Example B-2 | 1000 | 1292 | 5000 | Polyoxyethylene (10) lauryl ether acetic acid | 77 |
| Example B-3 | 1000 | 1292 | 5000 | Polyoxyethylene (10) lauryl ether acetic acid | 15 |
| Example B-4 | 1000 | 1292 | 5000 | Polyoxyethylene (4.5) lauryl ether acetic acid | 154 |
| Example B-5 | 1000 | 1292 | 5000 | Polyoxyethylene (4.5) lauryl ether acetic acid | 77 |
| Example B-6 | 1000 | 1292 | 5000 | Polyoxyethylene (4.5) lauryl ether acetic acid | 15 |
| Example B-7 | 1000 | 1292 | 5000 | Polyoxyethylene (10) lauryl ether acetic acid | 154 |
| Example B-8 | 1000 | 1292 | 5000 | Polyoxyethylene (10) lauryl ether acetic acid | 154 |
| Example B-9 | 1000 | 1292 | 5000 | Polyoxyethylene (10) lauryl ether acetic acid | 154 |
| Example B-10 | 1000 | 1292 | 5000 | Polyoxyethylene (4.5) lauryl ether acetic acid | 154 |
| Example B-11 | 1000 | 1292 | 5000 | Polyoxyethylene (4.5) lauryl ether acetic acid | 154 |
| Example B-12 | 1000 | 1292 | 5000 | Polyoxyethylene (4.5) lauryl ether acetic acid | 154 |
| Example B-13 | 1000 | 1292 | 5000 | Polyoxyethylene (4.5) lauryl ether acetic acid | 154 |
| Example B-14 | 1000 | 9012 | 5012 | Polyoxyethylene (10) lauryl ether acetic acid | 621 |
| Example B-15 | 1000 | 9012 | 5012 | Polyoxyethylene (4.5) lauryl ether acetic acid | 621 |
| Example B-16 | 1000 | 389 | 3525 | Polyoxyethylene (10) lauryl ether acetic acid | 73 |
| Example B-17 | 1000 | 389 | 3525 | Polyoxyethylene (4.5) lauryl ether acetic acid | 73 |
| Example B-18 | 1000 | 8092 | 3517 | Polyoxyethylene (10) lauryl ether acetic acid | 420 |
| Example B-19 | 1000 | 8092 | 3517 | Polyoxyethylene (4.5) lauryl ether acetic acid | 420 |

| | Stabilizer/ concentration [ppm] upon sterilization test | | Chelating agent/ concentration [ppm] upon sterilization test | | Sterilization test (*Bacillus cereus*) [CFU/mL] | | | |
|---|---|---|---|---|---|---|---|---|
| | | | | | Starting time | After 5 minutes | After 10 minutes | After 30 minutes |
| Example B-1 | Pyrophosphoric acid | 31 | — | 0 | $7.2 \times 10^5$ | — | $2.0 \times 10^3$ | Less than 100 |
| Example B-2 | Pyrophosphoric acid | 31 | — | 0 | $7.2 \times 10^5$ | — | $1.5 \times 10^3$ | Less than 100 |
| Example B-3 | Pyrophosphoric acid | 31 | — | 0 | $7.2 \times 10^5$ | — | $4.2 \times 10^3$ | Less than 100 |
| Example B-4 | Pyrophosphoric acid | 31 | — | 0 | $7.2 \times 10^5$ | — | 500 | Less than 100 |
| Example B-5 | Pyrophosphoric acid | 31 | — | 0 | $7.2 \times 10^5$ | — | $1.5 \times 10^3$ | Less than 100 |
| Example B-6 | Pyrophosphoric acid | 31 | — | 0 | $7.2 \times 10^5$ | — | $4.6 \times 10^3$ | Less than 100 |
| Example B-7 | Pyrophosphoric acid | 31 | EDTA•2Na | 83 | $7.2 \times 10^5$ | — | $7.9 \times 10^3$ | Less than 100 |
| Example B-8 | Pyrophosphoric acid | 31 | EDTA•2NH$_4$ | 74 | $7.2 \times 10^5$ | — | $7.6 \times 10^3$ | Less than 100 |
| Example B-9 | Pyrophosphoric acid | 31 | Dipicolinic acid | 37 | $7.2 \times 10^5$ | — | $5.2 \times 10^3$ | Less than 100 |
| Example B-10 | Pyrophosphoric acid | 31 | EDTA•2Na | 83 | $7.2 \times 10^5$ | — | $7.1 \times 10^3$ | Less than 100 |
| Example B-11 | Pyrophosphoric acid | 31 | EDTA•2NH$_4$ | 74 | $7.2 \times 10^5$ | — | $7.2 \times 10^3$ | Less than 100 |
| Example B-12 | Pyrophosphoric acid | 31 | HEDP | 46 | $7.2 \times 10^5$ | — | $8.3 \times 10^3$ | Less than 100 |
| Example B-13 | Pyrophosphoric acid | 31 | Dipicolinic acid | 37 | $7.2 \times 10^5$ | — | $2.1 \times 10^3$ | Less than 100 |

TABLE B-3-continued

[Table 5]

| | | | | | | | | |
|---|---|---|---|---|---|---|---|---|
| Example B-14 | Pyrophosphoric acid | 31 | — | 0 | $7.2 \times 10^5$ | — | 500 | Less than 100 |
| Example B-15 | Pyrophosphoric acid | 31 | — | 0 | $7.2 \times 10^5$ | — | 100 | Less than 100 |
| Example B-16 | HEDP | 51 | — | 0 | $7.2 \times 10^5$ | $2.0 \times 10^3$ | — | Less than 100 |
| Example B-17 | HEDP | 51 | — | 0 | $7.2 \times 10^5$ | 600 | — | Less than 100 |
| Example B-18 | HEDP | 50 | — | 0 | $7.2 \times 10^5$ | — | $9.6 \times 10^3$ | Less than 100 |
| Example B-19 | HEDP | 50 | — | 0 | $7.2 \times 10^5$ | — | $9.0 \times 10^3$ | Less than 100 |

TABLE B-4

[Table 6]

| | Peracetic acid concentration [ppm] upon sterilization test | Hydrogen peroxide concentration [ppm] upon sterilization test | Acetic acid concentration [ppm] | Compounding agent/concentration [ppm] upon sterilization test | |
|---|---|---|---|---|---|
| Comp. Ex. B-1 | 1000 | 1292 | 5000 | — | 0 |
| Comp. Ex. B-2 | 1000 | 1292 | 5000 | Polyoxyethylene octyl ether acetic acid | 154 |
| Comp. Ex. B-3 | 1000 | 1292 | 5000 | Polyoxyethylene hexyl/octyl ether acetic acid | 154 |
| Comp. Ex. B-4 | 1000 | 1292 | 5000 | Polyoxyethylene oleyl ether acetic acid | 154 |
| Comp. Ex. B-5 | 1000 | 1292 | 5000 | Sodium polyoxyethylene lauryl ether sulfate | 154 |
| Comp. Ex. B-6 | 1000 | 1292 | 5000 | Sodium dodecyl sulfate | 154 |
| Comp. Ex. B-7 | 1000 | 1292 | 5000 | Polyoxyethylene (23) lauryl ether | 154 |
| Comp. Ex. B-8 | 1000 | 1292 | 5000 | Polyoxyethylene (20) cetyl ether | 154 |
| Comp. Ex. B-9 | 1000 | 1292 | 5000 | Polyoxyethylene (20) sorbitan monolaurate | 154 |
| Comp. Ex. B-10 | 1000 | 1292 | 5000 | Polyoxyethylene (8) octyl phenyl ether | 154 |
| Comp. Ex. B-11 | 1000 | 9012 | 5012 | — | 0 |
| Comp. Ex. B-12 | 1000 | 389 | 3525 | — | 0 |
| Comp. Ex. B-13 | 1000 | 8092 | 3517 | — | 0 |

| | Stabilizer/concentration [ppm] upon sterilization test | | Chelating agent/concentration [ppm] upon sterilization test | Sterilization test (*Bacillus cereus*) [CFU/mL] | | | |
|---|---|---|---|---|---|---|---|
| | | | | Starting time | After 5 minutes | After 10 minutes | After 30 minutes |
| Comp. Ex. B-1 | Pyrophosphoric acid | 31 | — | 0 | $7.2 \times 10^5$ | — | $3.1 \times 10^4$ | 500 |
| Comp. Ex. B-2 | Pyrophosphoric acid | 31 | — | 0 | $7.2 \times 10^5$ | — | $2.4 \times 10^4$ | Less than 100 |
| Comp. Ex. B-3 | Pyrophosphoric acid | 31 | — | 0 | $7.2 \times 10^5$ | — | $1.6 \times 10^4$ | Less than 100 |
| Comp. Ex. B-4 | Pyrophosphoric acid | 31 | — | 0 | $7.2 \times 10^5$ | — | $2.5 \times 10^4$ | Less than 100 |
| Comp. Ex. B-5 | Pyrophosphoric acid | 31 | — | 0 | $7.2 \times 10^5$ | — | $1.1 \times 10^4$ | Less than 100 |
| Comp. Ex. B-6 | Pyrophosphoric acid | 31 | — | 0 | $7.2 \times 10^5$ | — | $5.5 \times 10^4$ | 200 |
| Comp. Ex. B-7 | Pyrophosphoric acid | 31 | — | 0 | $7.2 \times 10^5$ | — | $2.8 \times 10^4$ | Less than 100 |
| Comp. Ex. B-8 | Pyrophosphoric acid | 31 | — | 0 | $7.2 \times 10^5$ | — | $5.5 \times 10^4$ | Less than 100 |
| Comp. Ex. B-9 | Pyrophosphoric acid | 31 | — | 0 | $7.2 \times 10^5$ | — | $2.6 \times 10^4$ | 100 |
| Comp. Ex. B-10 | Pyrophosphoric acid | 31 | — | 0 | $7.2 \times 10^5$ | — | $4.2 \times 10^4$ | 300 |
| Comp. Ex. B-11 | Pyrophosphoric acid | 31 | — | 0 | $7.2 \times 10^5$ | — | $2.5 \times 10^4$ | Less than 100 |
| Comp. Ex. B-12 | HEDP | 51 | — | 0 | $7.2 \times 10^5$ | $8.0 \times 10^4$ | — | Less than 100 |
| Comp. Ex. B-13 | HEDP | 50 | — | 0 | $7.2 \times 10^5$ | — | $1.7 \times 10^5$ | Less than 100 |

TABLE B-5

[Table 7]

| | Peracetic acid concentration [ppm] upon test | Hydrogen peroxide concentration [ppm] upon test | Acetic acid concentration [ppm] | Compounding agent concentration [ppm] upon test | |
|---|---|---|---|---|---|
| Example B-1 | 200 | 258 | 1000 | Polyoxyethylene (10) lauryl ether acetic acid | 31 |
| Example B-3 | 200 | 258 | 1000 | Polyoxyethylene (10) lauryl ether acetic acid | 3 |
| Example B-4 | 200 | 258 | 1000 | Polyoxyethylene (4.5) lauryl ether acetic acid | 31 |

TABLE B-5-continued

[Table 7]

| | | | | | | |
|---|---|---|---|---|---|---|
| Example B-6 | 200 | 258 | 1000 | Polyoxyethylene (4.5) lauryl ether acetic acid | 3 |
| Comp. Ex. B-1 | 200 | 258 | 1000 | Non | | 0 |

| | Stabilizer/ concentration [ppm] upon test | Chelating agent/ concentration [ppm] upon test | | Scale removal amount [mg] | Scale removal amount [relative value] | Remaining protein amount [μg] | Remaining protein amount [relative value] |
|---|---|---|---|---|---|---|---|
| Example B-1 | Pyrophosphoric acid | 6 | — | 0 | 36.9 | 1.08 | — | — |
| Example B-3 | Pyrophosphoric acid | 6 | — | 0 | — | — | 16.3 | 0.89 |
| Example B-4 | Pyrophosphoric acid | 6 | — | 0 | 37.2 | 1.09 | — | — |
| Example B-6 | Pyrophosphoric acid | 6 | — | 0 | — | — | 18.2 | 0.99 |
| Comp. Ex. B-1 | Pyrophosphoric acid | 6 | — | 0 | 34.2 | 1.00 | 18.3 | 1.00 |

As described above, it was demonstrated that, according to the present invention, by adding a special anionic surfactant (polyoxyethylene lauryl ether acetic acid) to peracetic acid, a composition for sterilization and cleaning having improved stability and sterilizing ability compared with a conventional peracetic acid aqueous solution, and further having scale removal ability and protein removal ability, can be provided.

Embodiment C

Method of Measuring Hydrogen Peroxide Concentration in a Composition for Sterilization and Cleaning In the present invention, the concentration of the hydrogen peroxide in the composition for sterilization and cleaning (peracetic acid composition) was measured according to redox titration. Specifically, approximately 0.1 g of a sample was precisely weighed, and was then placed in a 250-mL Erlenmeyer flask. Then, 100 mL of pure water and 10 mL of 1.8 mol/L sulfuric acid were added thereto to prepare a test solution. Several drops of a ferroin indicator solution were added to this test solution, followed by titration with a 0.1 mol/L cerium(IV) sulfate solution, so that the hydrogen peroxide concentration was calculated.

Method for Measuring Acetic Acid and Peracetic Acid Concentrations in a Composition for Sterilization and Cleaning In the present invention, the concentrations of the acetic acid and the peracetic acid in the composition for sterilization and cleaning (peracetic acid composition) were measured according to neutralization titration. Specifically, approximately 0.1 g of a sample of the composition for sterilization and cleaning was precisely weighed, and was then placed in a 100-mL beaker. Then, approximately 50 mL of pure water was added thereto to prepare a test solution. This test solution was titrated with a 0.1 mol/L sodium hydroxide solution. Based on the additive amount at a first inflection point, the acetic acid concentration was calculated. Based on the additive amount from a first inflection point to a second inflection point, the peracetic acid concentration was calculated.

Total Peroxide (TPO) Concentration in a Composition for Sterilization and Cleaning In the present invention, the total concentration of peroxide in the composition for sterilization and cleaning (peracetic acid composition) was measured according to an iodometric method. Specifically, approximately 0.1 g of a sample was precisely weighed, and was then placed in a 250-mL Erlenmeyer flask. Then, 100 mL of pure water and 10 mL of 1.8 mol/L sulfuric acid were added thereto, and thereafter, 10 mL of a solution containing 10% by mass of potassium iodide and several drops of a solution containing 1% by mass of ammonium molybdate were added to the mixture to prepare a test solution. A 0.1 mol/L sodium thiosulfate solution was added dropwise to this test solution. Using starch as an indicator agent, a point at which a bluish-purple color disappeared from the solution and the solution became colorless was determined as an end point, and free iodine was quantified. Based on the amount of the iodine, the total peroxide concentration was calculated, in terms of hydrogen peroxide.

Stability of a Composition for Sterilization and Cleaning

The total peroxide (TPO) concentration at the time of the addition was set at 100, and the stability of the composition for sterilization and cleaning (peracetic acid composition) of the present invention was then calculated based on the ratio of the total peroxide concentration upon the measurement.

Preparation of a Spore Suspension

A *Bacillus cereus* standard strain (manufactured by Microbiologics, product name: *Bacillus cereus* ATCC10876) was coated onto an NGKG agar medium (manufactured by AZONE, product name: SANI-SPEC raw medium), and was then cultured at 35° C. for 7 days. Thereafter, sterile distilled water was added to the resulting agar medium, and a cell mass was then collected by scraping with a cell spreader. Thereafter, the cell mass was washing with sterile distilled water through centrifugation. In order to obtain only the spores, the resultant was heated at 80° C. for 10 minutes, and the surviving cells were prepared as a spore suspension.

Sterilization Test

The composition for sterilization and cleaning of the present invention (peracetic acid composition) was 40 to 300 times diluted with sterile distilled water to prepare a sample solution, in which the peracetic acid concentration became 90 to 200 ppm. Thereafter, 50 μL of the spore suspension was added to 5 mL of each sample solution, so that the sample solution was allowed to act on the spore suspension at 25° C. for 120 minutes. After completion of the action, the resulting solution was 10 times diluted with a 0.1 mol/L sterile sodium thiosulfate solution, and the diluted solution was then cultured at 35° C. for 48 hours, using a *Bacillus cereus* detection medium (manufactured by NIS SUI PHARMACEUTICAL CO., LTD., product name: Compact Dry X-BC). Thereafter, the number of living cells was measured. On the other hand, the number of living cells in the spore suspension was measured, and it was defined to be the number of living cells at the starting time of the test.

Example C-1

Pure water (22.0 g), 0.17 g of 60% by mass of 1-hydroxyethylidene-1,1-diphosphonic acid (HEDP, manufactured by Italmatch Japan, product name: D-Quest 2010), 0.11 g of ethylenediaminetetraacetic acid disodium dihydrate (EDTA.2Na. $2H_2O$, manufactured by MP Biomedicals, Inc.), 18.0 g of glacial acetic acid (manufactured by Showa Denko K. K., product name: 99% Pure and Good Acetic Acid), 45.6 g of sodium acetate trihydrate (manufactured by FUJIFILM Wako Pure Chemical Corporation), and 14.2 g of 45% by mass of a hydrogen peroxide solution (manufactured by Mitsubishi Gas Chemical Company, Inc., product name: SER45) were mixed in a PE container. Upon the mixing, the total peroxide concentration was 6.1%. After completion of the mixing, the mixture was maturated at 25° C. for 7 days, so as to obtain a peracetic acid composition for use in the cleaning of dialyzers, which comprised 5.6% by mass of hydrogen peroxide, 17.1% by mass of acetic acid, 1.1% by mass of peracetic acid, 0.1% by mass of 1-hydroxyethylidene-1,1-diphosphonic acid (HEDP), and 0.1% by mass of ethylenediaminetetraacetic acid disodium salt (EDTA.2Na), and having a pH of 5.1. Regarding the obtained peracetic acid composition, the total peroxide (TPO) concentration was measured at 25° C. 14 days after the formulation thereof, and the stability was then calculated. The results are shown in Table C-1 (shown in [Table 8]). The stability was evaluated as follows:
A: 94.5% or more (good);
B: 93.8% or more and less than 94.5% (practical); and
C: less than 93.8% (impractical).

Examples C-2 to C-14 and Comparative Examples C-1 to C-6

Compositions for sterilization and cleaning each having the concentration shown in Table C-1 were obtained in the same manner as that of Example C-1, with the exception that the additives shown in Table C-1 were used. Regarding the obtained compositions for sterilization and cleaning, the total peroxide (TPO) concentration was measured, and the stability was then calculated. The results are shown in Table C-1. DTPP, Na stannate.$3H_2O$, and DTPA shown in the table indicate the following products, respectively.
Diethylenetriamine penta(methylene phosphonic acid) (DTPP, manufactured by Mitsubishi Gas Chemical Company, Inc., refined product)
Sodium stannate trihydrate (Na stannate.$3H_2O$, manufactured by FUJIFILM Wako Pure Chemical Corporation)
Diethylenetriamine pentaacetic acid (DTPA, manufactured by DOJINDO LABORATORIES)

Examples C-15 to C-20

Compositions for sterilization and cleaning each having the concentration shown in Table C-2 (shown in [Table 9]) were obtained in the same manner as that of Example C-1, with the exceptions that the formulation as shown in Table C-2 was applied, and that maturation was carried out at 50° C. for 1 day. After the formulation thereof, the obtained compositions for sterilization and cleaning were maturated at 50° C. for 1 day and were left at 25° C. for 20 days. Thereafter, the total peroxide (TPO) concentration was measured, and the stability was then calculated. The results are shown in Table C-2. The stability was evaluated as follows:
A: 93.0% or more (good);
B: 90.0% or more and less than 93.0% (practical); and
C: less than 90.0% (impractical).

Examples C-21 and C-22 and Comparative Examples C-7 to C-12

Compositions for sterilization and cleaning each having the concentration shown in Table C-3 (shown in [Table 10]) were obtained in the same manner as that of Example C-1, with the exceptions that the formulation as shown in Table C-3 was applied, and that maturation was carried out at 25° C. for 21 day. The obtained compositions for sterilization and cleaning were left at 25° C. for 21 days after the formulation thereof. Thereafter, the total peroxide (TPO) concentration was measured, and the stability was then calculated. The results are shown in Table C-3. The stability was evaluated as follows:
A: 98.0% or more (good);
B: 96.0% or more and less than 98.0% (practical); and
C: less than 96.0% (impractical).
50% Phytic acid and NaOH shown in the table indicate the following products.
50 mass %-phytic acid solution (50% phytic acid, manufactured by FUJIFILM Wako Pure Chemical Corporation)
Sodium hydroxide (NaOH, manufactured by FUJIFILM Wako Pure Chemical Corporation)

Examples C-23 to C-25 and Comparative Examples C-13 and C-14

Compositions for sterilization and cleaning each having the concentration shown in Table C-4 (shown in [Table 11]) were obtained in the same manner as that of Example C-21, with the exception that the formulation as shown in Table C-4 was applied. The obtained compositions for sterilization and cleaning were left at 25° C. for 21 days after the formulation thereof. Thereafter, the total peroxide (TPO) concentration was measured, and the stability was then calculated. The results are shown in Table C-4. The stability was evaluated as follows:
A: 97.0% or more (good);
B: 94.0% or more and less than 97.0% (practical); and
C: less than 94.0% (impractical).
Pyrophosphoric acid shown in the table indicates the following product.
Pyrophosphoric acid (manufactured by Junsei Chemical Co., Ltd., product name: Diphosphoric Acid)

Comparative Examples C-15 to C-21

Compositions for sterilization and cleaning each having the concentration shown in Table C-5 (shown in [Table 12]) were obtained in the same manner as that of Example C-21, with the exceptions that the formulation as shown in Table C-5 was applied, and that maturation was carried out at 25° C. for 11 day. The obtained compositions for sterilization and cleaning were left at 25° C. for 21 days after the formulation thereof. Thereafter, the total peroxide (TPO) concentration was measured, and the stability was then calculated. The results are shown in Table C-5. The stability was evaluated as follows:
A: 97.0% or more (good);
B: 93.0% or more and less than 97.0% (practical); and
C: less than 93.0% (impractical).

Dipicolinic acid and EDTMP shown in the table indicate the following products.

Dipicolinic acid (manufactured by FUJIFILM Wako Pure Chemical Corporation)

Ethylenediamine tetra(methylene phosphonic acid) (EDTMP, manufactured by Tokyo Chemical Industry Co., Ltd.)

TABLE C-1

[Table 8]

| | Formulation | | | | | | | | |
|---|---|---|---|---|---|---|---|---|---|
| | Water [g] | 60 mass %-HEDP [g] | 10.5 mass %-DTPP [g] | EDTA·2Na·2H$_2$O [g] | DTPA [g] | Na stannate·3H$_2$O [g] | 99 mass %-glacial acetic acid [g] | 45 mass %-hydrogen peroxide solution [g] | Sodium acetate trihydrate [g] |
| Example C-1 | 22.0 | 0.17 | 0.00 | 0.11 | 0.00 | 0.00 | 18.0 | 14.2 | 45.6 |
| Example C-2 | 22.1 | 0.09 | 0.00 | 0.06 | 0.00 | 0.00 | 18.0 | 14.2 | 45.6 |
| Example C-3 | 22.2 | 0.02 | 0.00 | 0.01 | 0.00 | 0.00 | 18.0 | 14.2 | 45.6 |
| Example C-4 | 22.1 | 0.00 | 0.00 | 0.00 | 0.00 | 0.15 | 18.0 | 14.2 | 45.6 |
| Example C-5 | 21.9 | 0.17 | 0.00 | 0.00 | 0.00 | 0.15 | 18.0 | 14.2 | 45.6 |
| Example C-6 | 21.9 | 0.00 | 0.00 | 0.11 | 0.00 | 0.15 | 18.0 | 14.2 | 45.6 |
| Example C-7 | 21.8 | 0.17 | 0.00 | 0.11 | 0.00 | 0.15 | 18.0 | 14.2 | 45.6 |
| Example C-8 | 21.9 | 0.17 | 0.00 | 0.00 | 0.10 | 0.00 | 18.0 | 14.2 | 45.6 |
| Example C-9 | 21.1 | 0.00 | 0.95 | 0.11 | 0.00 | 0.00 | 18.0 | 14.2 | 45.6 |
| Example C-10 | 21.8 | 0.17 | 0.00 | 0.00 | 0.10 | 0.15 | 18.0 | 14.2 | 45.6 |
| Example C-11 | 21.4 | 0.50 | 0.00 | 0.33 | 0.00 | 0.00 | 18.0 | 14.2 | 45.6 |
| Example C-12 | 21.6 | 0.50 | 0.00 | 0.11 | 0.00 | 0.00 | 18.0 | 14.2 | 45.6 |
| Example C-13 | 21.7 | 0.17 | 0.00 | 0.33 | 0.00 | 0.00 | 18.0 | 14.2 | 45.6 |
| Example C-14 | 21.9 | 0.00 | 0.00 | 0.00 | 0.00 | 0.30 | 18.0 | 14.2 | 45.6 |
| Comp. Ex. C-1 | 22.1 | 0.17 | 0.00 | 0.00 | 0.00 | 0.00 | 18.0 | 14.2 | 45.6 |
| Comp. Ex. C-2 | 21.9 | 0.33 | 0.00 | 0.00 | 0.00 | 0.00 | 18.0 | 14.2 | 45.6 |
| Comp. Ex. C-3 | 22.0 | 0.00 | 0.00 | 0.22 | 0.00 | 0.00 | 18.0 | 14.2 | 45.6 |
| Comp. Ex. C-4 | 21.1 | 0.17 | 0.95 | 0.00 | 0.00 | 0.00 | 18.0 | 14.2 | 45.6 |
| Comp. Ex. C-5 | 22.0 | 0.00 | 0.00 | 0.11 | 0.10 | 0.00 | 18.0 | 14.2 | 45.6 |
| Comp. Ex. C-6 | 20.8 | 0.84 | 0.00 | 0.55 | 0.00 | 0.00 | 18.0 | 14.2 | 45.6 |

| | TPO concentration upon formulation [wt %] | Maturation at 25° C. for 7 days after formulation | | | | | | | | | | |
|---|---|---|---|---|---|---|---|---|---|---|---|---|
| | | Peracetic acid [wt %] | Hydrogen peroxide [wt %] | Acetic acid [wt %] | Na acetate [wt %] | Phosphorus-based | | Carboxylic acid-based | | Na stannate [wt %] | pH | Stability |
| | | | | | | HEDP [wt %] | DIPP [wt %] | EDTA·2Na [wt %] | DTPA [wt %] | | | |
| Example C-1 | 6.1 | 1.1 | 5.6 | 17.1 | 27.5 | 0.10 | 0.00 | 0.10 | 0.00 | 0.00 | 5.1 | A |
| Example C-2 | 6.1 | 1.1 | 5.5 | 17.1 | 27.5 | 0.05 | 0.00 | 0.05 | 0.00 | 0.00 | 5.1 | A |
| Example C-3 | 6.1 | 1.1 | 5.6 | 17.0 | 27.5 | 0.01 | 0.00 | 0.01 | 0.00 | 0.00 | 5.1 | A |
| Example C-4 | 6.1 | 1.1 | 5.5 | 16.9 | 27.5 | 0.00 | 0.00 | 0.00 | 0.00 | 0.10 | 5.1 | A |
| Example C-5 | 6.1 | 1.0 | 5.6 | 17.0 | 27.5 | 0.10 | 0.00 | 0.00 | 0.00 | 0.10 | 5.1 | A |
| Example C-6 | 6.1 | 1.1 | 5.5 | 17.0 | 27.5 | 0.00 | 0.00 | 0.10 | 0.00 | 0.10 | 5.1 | A |
| Example C-7 | 6.1 | 1.1 | 5.6 | 17.1 | 27.5 | 0.10 | 0.00 | 0.10 | 0.00 | 0.10 | 5.1 | A |
| Example C-8 | 6.1 | 1.0 | 5.5 | 17.2 | 27.5 | 0.10 | 0.00 | 0.00 | 0.10 | 0.00 | 5.1 | B |
| Example C-9 | 6.1 | 1.1 | 5.6 | 17.2 | 27.5 | 0.00 | 0.10 | 0.10 | 0.00 | 0.00 | 5.1 | A |
| Example C-10 | 6.1 | 1.0 | 5.6 | 17.0 | 27.5 | 0.10 | 0.00 | 0.00 | 0.10 | 0.10 | 5.1 | A |
| Example C-11 | 6.1 | 1.0 | 5.5 | 17.6 | 27.5 | 0.30 | 0.00 | 0.30 | 0.00 | 0.00 | 5.1 | B |
| Example C-12 | 6.1 | 1.0 | 5.5 | 17.4 | 27.5 | 0.30 | 0.00 | 0.10 | 0.00 | 0.00 | 5.1 | A |
| Example C-13 | 6.1 | 1.1 | 5.5 | 17.1 | 27.5 | 0.10 | 0.00 | 0.30 | 0.00 | 0.00 | 5.1 | B |
| Example C-14 | 6.1 | 1.1 | 5.5 | 16.9 | 27.5 | 0.00 | 0.00 | 0.00 | 0.00 | 0.20 | 5.1 | B |
| Comp. Ex. C-1 | 6.1 | 1.0 | 5.5 | 17.2 | 27.5 | 0.10 | 0.00 | 0.00 | 0.00 | 0.00 | 5.1 | C |
| Comp. Ex. C-2 | 6.1 | 1.0 | 5.5 | 17.3 | 27.5 | 0.20 | 0.00 | 0.00 | 0.00 | 0.00 | 5.1 | C |
| Comp. Ex. C-3 | 6.1 | 1.0 | 5.5 | 17.2 | 27.5 | 0.00 | 0.00 | 0.20 | 0.00 | 0.00 | 5.1 | C |
| Comp. Ex. C-4 | 6.1 | 1.0 | 5.5 | 17.3 | 27.5 | 0.10 | 0.10 | 0.00 | 0.00 | 0.00 | 5.1 | C |
| Comp. Ex. C-5 | 6.1 | 1.0 | 5.5 | 17.1 | 27.5 | 0.00 | 0.00 | 0.10 | 0.10 | 0.00 | 5.1 | C |
| Comp. Ex. C-6 | 6.1 | 1.2 | 5.4 | 17.6 | 27.5 | 0.50 | 0.00 | 0.50 | 0.00 | 0.00 | 5.1 | C |

TABLE C-2-1

[Table 9-1]

| | | Formulation | | | | | | |
|---|---|---|---|---|---|---|---|---|
| | | Carboxylic acid-based | | Phosphorus-based | | 99 mass %-glacial acetic acid [g] | 45 mass %-hydrogen peroxide solution [g] | Sodium acetate trihydrate [g] | TPO concentration upon formulation [wt %] |
| | Water [g] | Type | Additive amount [g] | Type | Additive amount [g] | | | | |
| Example C-15 | 24.6 | EDTA•2Na•2H$_2$O | 0.11 | 60 mass %-HEDP | 0.17 | 9.5 | 14.0 | 51.7 | 6.1 |
| Example C-16 | 21.5 | EDTA•2Na•2H$_2$O | 0.11 | 60 mass %-HEDP | 0.17 | 10.5 | 14.2 | 53.5 | 6.1 |
| Example C-17 | 28.6 | EDTA•2Na•2H$_2$O | 0.11 | 60 mass %-HEDP | 0.17 | 14.5 | 14.2 | 42.4 | 6.1 |
| Example C-18 | 22.0 | EDTA•2Na•2H$_2$O | 0.11 | 60 mass %-HEDP | 0.17 | 18.0 | 14.2 | 45.6 | 6.1 |
| Example C-19 | 25.5 | EDTA•2Na•2H$_2$O | 0.11 | 60 mass %-HEDP | 0.17 | 8.1 | 17.5 | 48.6 | 7.6 |
| Example C-20 | 21.1 | EDTA•2Na•2H$_2$O | 0.11 | 60 mass %-HEDP | 0.17 | 8.1 | 21.9 | 48.6 | 9.5 |

TABLE C-2-2

[Table 9-2]

| | Maturation at 50° C. for 1 day after formulation | | | | | | | | |
|---|---|---|---|---|---|---|---|---|---|
| | Peracetic acid [wt %] | Hydrogen peroxide [wt %] | Acetic acid [wt %] | Na acetate [wt %] | Carboxylic acid-based | | Phosphorus-based | | |
| | | | | | Type | Concentration [wt %] | Type | Concentration [wt %] | pH | Stability |
| Example C-15 | 0.58 | 5.8 | 9.1 | 31.1 | EDTA•2Na | 0.10 | HEDP | 0.10 | 5.5 | A |
| Example C-16 | 0.61 | 5.8 | 10.2 | 32.2 | EDTA•2Na | 0.10 | HEDP | 0.10 | 5.5 | A |
| Example C-17 | 0.9 | 5.8 | 13.9 | 25.6 | EDTA•2Na | 0.10 | HEDP | 0.10 | 5.1 | A |
| Example C-18 | 1.13 | 5.6 | 17.3 | 27.5 | EDTA•2Na | 0.10 | HEDP | 0.10 | 5.1 | B |
| Example C-19 | 0.62 | 7.2 | 7.8 | 29.3 | EDTA•2Na | 0.10 | HEDP | 0.10 | 5.4 | A |
| Example C-20 | 0.76 | 8.7 | 7.7 | 29.3 | EDTA•2Na | 0.10 | HEDP | 0.10 | 5.4 | B |

TABLE C-3-1

[Table 10-1]

| | Formulation | | | | | | | |
|---|---|---|---|---|---|---|---|---|
| | | Carboxylic acid-based | | Phosphorus-based 1 | | Phosphorus-based 2 | | |
| | Water [g] | Type | Additive amount [g] | Type | Additive amount [g] | Type | Additive amount [g] | |
| Example C-21 | 34.5 | EDTA•2Na•2H$_2$O | 0.06 | 60 mass %-HEDP | 0.09 | — | 0.00 | |
| Example C-22 | 34.5 | — | 0.00 | — | 0.00 | — | 0.00 | |
| Comp. Ex. C-7 | 34.5 | — | 0.00 | 60 mass %-HEDP | 0.09 | — | 0.00 | |
| Comp. Ex. C-8 | 34.4 | — | 0.00 | 60 mass %-HEDP | 0.18 | — | 0.00 | |
| Comp. Ex. C-9 | 34.6 | DTPA | 0.06 | — | 0.00 | — | 0.00 | |
| Comp. Ex. C-10 | 34.5 | — | 0.00 | 50% Phytic acid | 0.11 | — | 0.00 | |
| Comp. Ex. C-11 | 34.0 | — | 0.00 | 60 mass %-HEDP | 0.09 | 10.5 mass %-DTPP | 0.50 | |
| Comp. Ex. C-12 | 34.5 | — | 0.00 | 60 mass %-HEDP | 0.09 | Pyrophosphoric acid | 0.06 | |

| | Formulation | | | | | |
|---|---|---|---|---|---|---|
| | Others | | 99 mass %-glacial acetic acid [g] | 45 mass %-hydrogen peroxide solution [g] | NaOH [g] | TPO concentration upon formulation [wt %] |
| | Type | Additive amount [g] | | | | |
| Example C-21 | — | 0.00 | 8.4 | 6.9 | 3.8 | 5.6 |
| Example C-22 | Na stannate•3H$_2$O | 0.07 | 8.4 | 6.9 | 3.8 | 5.6 |
| Comp. Ex. C-7 | — | 0.00 | 8.4 | 6.9 | 3.8 | 5.6 |

TABLE C-3-1-continued

[Table 10-1]

| | | | | | | |
|---|---|---|---|---|---|---|
| Comp. Ex. C-8 | — | 0.00 | 8.4 | 6.9 | 3.8 | 5.6 |
| Comp. Ex. C-9 | — | 0.00 | 8.4 | 6.9 | 3.8 | 5.6 |
| Comp. Ex. C-10 | — | 0.00 | 8.4 | 6.9 | 3.8 | 5.6 |
| Comp. Ex. C-11 | — | 0.00 | 8.4 | 6.9 | 3.8 | 5.6 |
| Comp. Ex. C-12 | — | 0.00 | 8.4 | 6.9 | 3.8 | 5.6 |

TABLE C-3-2

[Table 10-2]

Maturation at 25° C. for 21 days after formulation

| | Peracetic acid [wt %] | Hydrogen peroxide [wt %] | Acetic acid [wt %] | Na acetate [wt %] | Carboxylic acid-based Type | Carboxylic acid-based Concentration [wt %] | Phosphorus-based 1 Type | Phosphorus-based 1 Concentration [wt %] |
|---|---|---|---|---|---|---|---|---|
| Example C-21 | 0.29 | 5.44 | 5.11 | 15.6 | EDTA•2Na | 0.10 | HEDP | 0.10 |
| Example C-22 | 0.29 | 5.37 | 5.05 | 15.6 | — | 0.00 | — | 0.00 |
| Comp. Ex. C-7 | 0.21 | 4.97 | 5.39 | 15.6 | — | 0.00 | HEDP | 0.10 |
| Comp. Ex. C-8 | 0.22 | 5.02 | 5.33 | 15.6 | — | 0.00 | HEDP | 0.20 |
| Comp. Ex. C-9 | 0.25 | 5.22 | 5.4 | 15.6 | DTPA | 0.10 | — | 0.00 |
| Comp. Ex. C-10 | 0.15 | 4.46 | 5.23 | 15.6 | — | 0.00 | Phytic acid | 0.10 |
| Comp. Ex. C-11 | 0.21 | 5.01 | 5.39 | 15.6 | — | 0.00 | HEDP | 0.10 |
| Comp. Ex. C-12 | 0.21 | 5.04 | 5.34 | 15.6 | — | 0.00 | HEDP | 0.10 |

Maturation at 25° C. for 21 days after formulation

| | Phosphorus-based 2 Type | Phosphorus-based 2 Concentration [wt %] | Others Type | Others Concentration [wt %] | pH | Stability |
|---|---|---|---|---|---|---|
| Example C-21 | — | 0.00 | — | 0.00 | 5.0 | A |
| Example C-22 | — | 0.00 | Na stannate | 0.10 | 5.0 | A |
| Comp. Ex. C-7 | — | 0.00 | — | 0.00 | 5.0 | C |
| Comp. Ex. C-8 | — | 0.00 | — | 0.00 | 5.0 | C |
| Comp. Ex. C-9 | — | 0.00 | — | 0.00 | 5.0 | C |
| Comp. Ex. C-10 | — | 0.00 | — | 0.00 | 5.0 | C |
| Comp. Ex. C-11 | DTPP | 0.10 | — | 0.00 | 5.0 | C |
| Comp. Ex. C-12 | Pyrophosphoric acid | 0.10 | — | 0.00 | 5.0 | C |

TABLE C-4

Table 11

Formulation

| | Water [g] | Carboxylic acid-based Type | Carboxylic Additive amount [g] | Phosphorus-based Type | Phosphorus-based Additive amount [g] | 99 mass %- glacial acetic acid [g] | 45 mass %- hydrogen peroxide solution [g] | NaOH [g] | TPO concentration upon formulation [wt %] |
|---|---|---|---|---|---|---|---|---|---|
| Example C-23 | 30.8 | EDTA•2Na•2H$_2$O | 0.06 | 60 mass %-HEDP | 0.09 | 11.8 | 7.3 | 5.2 | 5.7 |
| Example C-24 | 30.3 | EDTA•2Na•2H$_2$O | 0.06 | 10.5 mass %-DTPP | 0.50 | 11.8 | 7.3 | 5.2 | 5.7 |
| Example C-25 | 30.8 | EDTA•2Na•2H$_2$O | 0.06 | Pyrophosphoric acid | 0.06 | 11.8 | 7.3 | 5.2 | 5.7 |
| Comp. Ex. C-13 | 30.8 | EDTA•2Na•2H$_2$O | 0.06 | — | 0.00 | 11.8 | 7.3 | 5.2 | 5.7 |
| Comp. Ex. C-14 | 30.8 | EDTA•2Ka•2H$_2$O | 0.12 | — | 0.00 | 11.8 | 7.3 | 5.2 | 5.7 |

TABLE C-4-continued

Table 11

Maturation at 25° C. for 21 days after formulation

| | Peracetic acid [wt %] | Hydrogen peroxide [wt %] | Acetic acid [wt %] | Na acetate [wt %] | Carboxylic acid-based Type | Concentration [wt %] | Phosphorus-based Type | Concentration [wt %] | pH | Stability |
|---|---|---|---|---|---|---|---|---|---|---|
| Example C-23 | 0.41 | 5.4 | 7.3 | 21.1 | EDTA•2Na | 0.10 | HEDP | 0.10 | 5.0 | A |
| Example C-24 | 0.40 | 5.3 | 7.5 | 21.1 | EDTA•2Na | 0.10 | DTPP | 0.10 | 5.0 | B |
| Example C-25 | 0.42 | 5.3 | 7.4 | 21.1 | EDTA•2Na | 0.10 | Pyrophosphonc acid | 0.10 | 5.0 | B |
| Comp. Ex. C-13 | 0.36 | 5.1 | 7.3 | 21.1 | EDTA•2Na | 0.10 | — | 0.00 | 5.0 | C |
| Comp. Ex. C-14 | 0.41 | 5.2 | 7.3 | 21.1 | EDTA•2Na | 0.20 | — | 0.00 | 5.0 | C |

TABLE C-5

Table 12

Formulation

| | Water [g] | Carboxylic acid-based Type | Additive amount [g] | Phosphorus-based Type | Additive amount [g] | 99 mass %-glacial acetic acid [g] | 45 mass %-hydrogen peroxide solution [g] | NaOH [g] | TPO concentration upon formulation [wt %] |
|---|---|---|---|---|---|---|---|---|---|
| Comp. Ex. C-15 | 37.85 | — | 0.00 | — | 0.00 | 5.3 | 6.9 | 2.8 | 5.6 |
| Comp. Ex. C-16 | 37.80 | — | 0.00 | Pyrophosphoric acid | 0.05 | 5.3 | 6.9 | 2.8 | 5.6 |
| Comp. Ex C-17 | 37.77 | — | 0.00 | 60 mass %-HEDP | 0.08 | 5.3 | 6.9 | 2.8 | 5.6 |
| Comp. Ex. C-18 | 37.79 | EDTA•2Na•2H₂O | 0.06 | — | 0.00 | 5.3 | 6.9 | 2.8 | 5.6 |
| Comp. Ex C-19 | 37.80 | Dipicolinic acid | 0.05 | — | 0.00 | 5.3 | 6.9 | 2.8 | 5.6 |
| Comp. Ex. C-20 | 37.35 | — | 0.00 | 10.5 mass %-DTPP | 0.50 | 5.3 | 6.9 | 2.8 | 5.6 |
| Comp. Ex. C-21 | 37.80 | — | 0.05 | EDTMP | 0.00 | 5.3 | 6.9 | 2.8 | 5.6 |

Maturation at 25° C. for 11 days after formulation

| | Peracetic acid [wt %] | Hydrogen peroxide [wt %] | Acetic acid [wt %] | Na acetate [wt %] | Carboxylic acid-based Type | Concentration [wt %] | Phosphorus-based Type | Concentration [wt %] | pH | Stability |
|---|---|---|---|---|---|---|---|---|---|---|
| Comp. Ex. C-15 | 0.00 | 1.0 | 2.3 | 11.4 | — | 0.00 | — | 0.00 | 5.0 | C |
| Comp. Ex. C-16 | 0.15 | 5.5 | 2.3 | 11.4 | — | 0.00 | Pyrophosphoric acid | 0.10 | 5.0 | C |
| Comp. Ex C-17 | 0.17 | 5.4 | 2.3 | 11.4 | — | 0.00 | HEDP | 0.10 | 5.0 | C |
| Comp. Ex. C-18 | 0.19 | 5.5 | 2.2 | 11.4 | EDTA•2Na | 0.10 | — | 0.00 | 5.0 | C |
| Comp. Ex C-19 | 0.06 | 5.1 | 2.4 | 11.4 | Dipicolinic acid | 0.10 | — | 0.00 | 5.0 | C |
| Comp. Ex. C-20 | 0.17 | 5.5 | 2.3 | 11.4 | — | 0.10 | DTPP | 0.10 | 5.0 | C |
| Comp. Ex. C-21 | 0.10 | 5.4 | 2.3 | 11.4 | — | 0.10 | EDTMP | 0.10 | 5.0 | C |

Examples C-26 to C-29

The results obtained by examining the methods for producing the composition for sterilization and cleaning of the present invention are shown, as examples, in Table C-6 (shown in [Table 13]) below. In Examples C-26 and C-28 in which alkali was used, an increase in the reaction speed by a heat of neutralization was observed, in comparison to Examples C-27 and C-29 in which acetate was used.

TABLE C-6

[Table 13]

| | | Formulation | | | | | | | |
|---|---|---|---|---|---|---|---|---|---|
| | | Carboxylic acid-based | | Phosphorus-based | | 99 mass %-glacial acetic acid [g] | 45 mass % hydrogen peroxide solution [g] | NaOH [g] | Sodium acetate trihydrate [g] |
| | Water [g] | Type | Additive amount [g] | Type | Additive amount [g] | | | | |
| Example C-26 | 49.6 | EDTA•2Na•2H$_2$O | 0.11 | 60 mass %-HEDP | 0.17 | 24.8 | 13.4 | 12.0 | 0.0 |
| Example C-27 | 38.8 | EDTA•2Na•2H$_2$O | 0.11 | 60 mass %-HEDP | 0.17 | 6.8 | 13.4 | 0.0 | 40.7 |
| Example C-28 | 42.4 | EDTA•2Na•2H$_2$O | 0.11 | 60 mass %-HEDP | 0.17 | 29.6 | 13.4 | 14.3 | 0.0 |
| Example C-29 | 29.6 | EDTA•2Na•2H$_2$O | 0.11 | 60 mass %-HEDP | 0.17 | 8.1 | 13.4 | 0.0 | 48.7 |

| | Maturation at 25° C. after formulation | | | | | | | | |
|---|---|---|---|---|---|---|---|---|---|
| | Peracetic acid [wt %] | Hydrogen peroxide [wt %] | Acetic acid [wt %] | Na acetate [wt %] | Carboxylic acid-based | | Phosphorus-based | | Days necessary for maturation [day] |
| | | | | | Type | Concentration [wt %] | Type | Concentration [wt %] | pH |
| Example C-26 | 0.34 | 5.6 | 6.8 | 24.5 | EDTA•2Na | 0.10 | HEDP | 0.10 | 5.3 | 6 |
| Example C-27 | 0.35 | 5.6 | 6.6 | 24.5 | EDTA•2Na | 0.10 | HEDP | 0.10 | 5.3 | 8 |
| Example C-28 | 0.39 | 5.6 | 8.2 | 29.3 | EDTA•2Na | 0.10 | HEDP | 0.10 | 5.6 | 4 |
| Example C-29 | 0.41 | 5.6 | 8.0 | 29.3 | EDTA•2Na | 0.10 | HEDP | 0.10 | 5.5 | 6 |

Example C-101

Pure water (20.0 g), 0.02 g of 60% by mass of 1-hydroxyethylidene-1,1-diphosphonic acid (HEDP, manufactured by Italmatch Japan, product name: D-Quest 2010), 0.01 g of ethylenediaminetetraacetic acid disodium dihydrate (EDTA.2Na. 2H$_2$O, manufactured by MP Biomedicals, Inc.), 28.4 g of 85% by mass of potassium hydroxide (manufactured by FUJIFILM Wako Pure Chemical Corporation), 37.4 g of glacial acetic acid (manufactured by Showa Denko K. K., product name: 99% Pure and Good Acetic Acid), and 14.2 g of 45% by mass of hydrogen peroxide (manufactured by Mitsubishi Gas Chemical Company, Inc., product name: SER45) were mixed in a PE container. The total peroxide concentration upon the mixing was 6.1%. After completion of the mixing, the mixture was maturated at 50° C. for 1 day and was then cooled to 25° C., so as to obtain a composition for sterilization and cleaning (peracetic acid composition), which comprised 5.7% by mass of hydrogen peroxide, 10.7% by mass of acetic acid, 0.33% by mass of peracetic acid, 44.7% by mass of potassium acetate, 0.01% by mass of 1-hydroxyethylidene-1,1-diphosphonic acid, and 0.01% by mass of ethylenediaminetetraacetic acid disodium salt, and having a pH of 5.1. A stability test was performed on the obtained composition for sterilization and cleaning (peracetic acid composition). The results are shown in Table C-7 (shown in [Table 14]).

Examples C-102 to C-104 and Comparative Example C-101

Compositions for sterilization and cleaning (peracetic acid compositions) were obtained in the same manner as that of Example C-101, with the exception that the formulation of Example C-101 was changed to the formulations each shown in Table C-7. A stability test was performed on the obtained compositions for sterilization and cleaning (peracetic acid compositions). The results are shown in Table C-7. The stability was evaluated as follows:

A: Good;

B: Practical; and

C: Impractical.

Disodium hydrogen phosphate dodecahydrate (manufactured by FUJIFILM Wako Pure Chemical Corporation)

Sodium citrate dodecahydrate (manufactured by FUJIFILM Wako Pure Chemical Corporation)

Tris(hydroxymethyl)aminomethane (alias: 2-amino-2-hydroxymethyl-1,3-propanediol, manufactured by FUJIFILM Wako Pure Chemical Corporation)

2-(4-(2-Hydroxyethyl)-1-piperazinyl)ethanesulfonic acid (HEPES, DOJINDO LABORATORIES)

TABLE C-7

[Table 14]

| | Formulation | | | | | | | |
|---|---|---|---|---|---|---|---|---|
| | | | | | pH adjuster | | | |
| No. | Water [g] | 99 mass %-glacial acetic acid [g] | 45 mass %-hydrogen peroxide solution [g] | 85 mass %-potassium hydroxide [g] | Disodium hydrogen phosphate dodecahydrate [g] | Sodium citrate dihydrate [g] | Tris(hydroxy-methyl)aminomethane [g] | HEPES [g] |
| Example C-101 | 20.0 | 37.4 | 14.2 | 28.4 | 0.0 | 0.0 | 0.0 | 0.0 |
| Example C-102 | 0.0 | 16.0 | 14.8 | 0.0 | 69.2 | 0.0 | 0.0 | 0.0 |
| Example C-103 | 31.6 | 20.0 | 14.8 | 8.1 | 0.5 | 25.0 | 0.0 | 0.0 |
| Example C-104 | 26.6 | 20.0 | 14.8 | 0.0 | 0.5 | 25.0 | 20.0 | 0.0 |
| Comp. Ex. C-101 | 29.3 | 16.0 | 14.8 | 0.0 | 0.0 | 0.0 | 0.0 | 40.0 |

| | Formulation | | TPO concentration upon formulation [wt %] | Maturation at 50° C. for 1 day after formulation | | | | |
|---|---|---|---|---|---|---|---|---|
| No. | 60 mass %-HEDP [g] | EDTA·2Na·2H₂O [g] | | Peracetic acid [wt %] | Hydrogen peroxide [wt %] | Acetic acid [wt %] | Potassium acetate [wt %] | Disodium hydrogen phosphate [wt %] |
| Example C-101 | 0.02 | 0.01 | 6.1 | 0.33 | 5.7 | 10.7 | 44.7 | 0.0 |
| Example C-102 | 0.02 | 0.01 | 6.4 | 0.50 | 6.0 | 15.9 | 0.0 | 27.4 |
| Example C-103 | 0.02 | 0.01 | 6.4 | 0.44 | 5.8 | 12.0 | 12.7 | 0.2 |
| Example C-104 | 0.02 | 0.01 | 6.4 | 0.19 | 3.7 | 12.4 | 0.0 | 0.2 |
| Comp. Ex. C-101 | 0.02 | 0.01 | 6.4 | 0.01 | 0.3 | 16.0 | 0.0 | 0.0 |

| | Maturation at 50° C. for 1 day after formulation | | | | | | | |
|---|---|---|---|---|---|---|---|---|
| No. | Sodium citrate [wt %] | Tris(hydroxy-methyl)amino-methane acetate [wt %] | HEPES [wt %] | Phosphorus-based HEDP [wt %] | Carboxylic acid-based EDTA·2Na [wt %] | pH | pH after 50-fold dilution | Stability |
| Example C-101 | 0.0 | 0.0 | 0.0 | 0.01 | 0.01 | 6.4 | 5.0 | A |
| Example C-102 | 0.0 | 0.0 | 0.0 | 0.01 | 0.01 | 4.9 | 5.1 | A |
| Example C-103 | 21.9 | 0.0 | 0.0 | 0.01 | 0.01 | 5.2 | 5.0 | A |
| Example C-104 | 21.9 | 29.9 | 0.0 | 0.01 | 0.01 | 5.1 | 5.1 | B |
| Comp. Ex. C-101 | 0.0 | 0.0 | 40.0 | 0.01 | 0.01 | 3.5 | 3.4 | C |

Example C-105

Pure water (22.2 g), 0.02 g of 60% by mass of 1-hydroxyethylidene-1,1-diphosphonic acid (HEDP, manufactured by Italmatch Japan, product name: D-Quest 2010), 0.01 g of ethylenediaminetetraacetic acid disodium dihydrate (EDTA.2Na. 2H₂O, manufactured by MP Biomedicals, Inc.), 18.0 g of ultrapure acetic acid (manufactured by KANTO CHEMICAL CO., INC., standard: Ultrapur), 45.6 g of sodium acetate trihydrate (manufactured by FUJIFILM Wako Pure Chemical Corporation), and 14.2 g of 45% by mass of a hydrogen peroxide solution (manufactured by Mitsubishi Gas Chemical Company, Inc., product name: SER45) were mixed in a PE container. The total peroxide concentration upon the mixing was 6.1%. After completion of the mixing, the mixture was maturated at 25° C. for 7 days, so as to obtain a composition for sterilization and cleaning (peracetic acid composition) comprising 5.6% by mass of hydrogen peroxide, 17.1% by mass of acetic acid, 1.0% by mass of peracetic acid, 0.01% by mass of 1-hydroxyethylidene-1,1-diphosphonic acid (HEDP), 0.01% by mass of ethylenediaminetetraacetic acid disodium salt (EDTA.2Na), and having a pH of 5.1. The obtained composition for sterilization and cleaning (peracetic acid composition) was left at 25° C. for 42 days after the formulation thereof. Thereafter, the total peroxide (TPO) concentration was measured, and the stability was then calculated. The results are shown in Table C-8 (shown in [Table 15]).

Examples C-106 to C-108

Compositions for sterilization and cleaning (peracetic acid compositions) were obtained in the same manner as that of Example C-105, with the exception that the formulation of Example C-105 was changed to the formulations each shown in Table C-8. A stability test was performed on the obtained compositions for sterilization and cleaning (peracetic acid compositions). The results are shown in Table C-8. The stability was evaluated as follows:

A: Good;

B: Practical; and

C: Impractical.

35 mass %-ultrapure hydrogen peroxide (manufactured by Mitsubishi Gas Chemical Company, Inc., product name: UELM35)

TABLE C-8

[Table 15]

| | | | Formulation | | | | | |
|---|---|---|---|---|---|---|---|---|
| No. | Water [g] | 99 mass %-glacial acetic acid [g] | 99 mass %-ultrapure acetic acid [g] | 45 mass %-hydrogen peroxide solution [g] | 35 mass %-ultrapure hydrogen peroxide [g] | Sodium acetate trihydrate [g] | 60 mass %-HEDP [g] | EDTA•2Na•2H$_2$O [g] |
| Example C-105 | 22.2 | 0.0 | 18.0 | 14.2 | 0.0 | 45.6 | 0.02 | 0.01 |
| Example C-106 | 18.9 | 18.0 | 0.0 | 0.0 | 17.5 | 45.6 | 0.02 | 0.01 |
| Example C-107 | 18.9 | 0.0 | 18.0 | 0.0 | 17.5 | 45.6 | 0.02 | 0.01 |
| Example C-108 | 22.2 | 18.0 | 0.0 | 14.2 | 0.0 | 45.6 | 0.02 | 0.01 |

| | | Maturation at 25° C. for 7 days after formulation | | | | | | | |
|---|---|---|---|---|---|---|---|---|---|
| No. | TPO concentration upon formulation [wt %] | Peracetic acid [wt %] | Hydrogen peroxide [wt %] | Acetic acid [wt %] | Na acetate [wt %] | Phosphorus-based HEDP [wt %] | Carboxylic acid-based EDTA•2Na [wt %] | pH | Stability |
| Example C-105 | 6.1 | 1.0 | 5.6 | 17.1 | 27.5 | 0.01 | 0.01 | 5.1 | A |
| Example C-106 | 6.1 | 1.1 | 5.6 | 17.1 | 27.5 | 0.01 | 0.01 | 5.1 | A |
| Example C-107 | 6.1 | 1.1 | 5.7 | 17.1 | 27.5 | 0.01 | 0.01 | 5.1 | A |
| Example C-108 | 6.1 | 1.1 | 5.6 | 17.0 | 27.5 | 0.01 | 0.01 | 5.1 | A |

Example C-109

Aluminum potassium sulfate dodecahydrate (1.8 g) (manufactured by FUJIFILM Wako Pure Chemical Corporation) was dissolved in 100 g of pure water to prepare an Al aqueous solution (Al: 1000 ppm). Pure water (31.0 g), 0.02 g of 60% by mass of 1-hydroxyethylidene-1,1-diphosphonic acid (HEDP, manufactured by Italmatch Japan, product name: D-Quest 2010), 0.01 g of ethylenediaminetetraacetic acid disodium dihydrate (EDTA-2Na-2H$_2$O, manufactured by MP Biomedicals, Inc.), 38.1 g of ultrapure acetic acid (manufactured by KANTO CHEMICAL CO., INC., standard: Ultrapur), 13.4 g of sodium hydroxide (manufactured by FUJIFILM Wako Pure Chemical Corporation), 17.5 g of 35% by mass of ultrapure hydrogen peroxide (manufactured by Mitsubishi Gas Chemical Company, Inc., product name: UELM35), and 0.005 g of the Al aqueous solution (1000 ppm) were mixed in a PE container. The total peroxide concentration upon the mixing was 6.1%. After the mixing, the mixture was maturated at 25° C. for 7 days, so as to obtain a composition for sterilization and cleaning (peracetic acid composition), which comprised 5.6% by mass of hydrogen peroxide, 17.5% by mass of acetic acid, 1.1% by mass of peracetic acid, 0.01% by mass of 1-hydroxyethylidene-1,1-diphosphonic acid (HEDP), and 0.01% by mass of ethylenediaminetetraacetic acid disodium salt (EDTA-2Na), and having a pH of 5.1. The obtained composition for sterilization and cleaning (peracetic acid composition) was left at 25° C. for 21 days after the formulation thereof. Thereafter, the total peroxide (TPO) concentration was measured, and the stability was then calculated. The results are shown in Table C-9 (shown in [Table 16]).

Examples C-110 to C-112 and Reference Example C-102

Compositions for sterilization and cleaning (peracetic acid compositions) were obtained in the same manner as that of Example C-109, with the exception that the formulation of Example C-109 was changed to the formulations each shown in Table C-9. A stability test was performed on the obtained compositions for sterilization and cleaning (peracetic acid compositions). The results are shown in Table C-9. The stability was evaluated as follows:
A: Good;
B: Practical; and
C: Impractical.
Zr standard solution (Zr: 1000 ppm) (manufactured by FUJIFILM Wako Pure Chemical Corporation)
Nb standard (Nb: 1000 ppm) (manufactured by FUJIFILM Wako Pure Chemical Corporation)

TABLE C-9

[Table 16]

| | Formulation | | | | | | | | |
|---|---|---|---|---|---|---|---|---|---|
| No. | Water [g] | 99 mass % ultrapure acetic acid [g] | 35 mass % ultrapure hydrogen peroxide [g] | Sodium hydroxide [g] | 60 mass %-HEDP [g] | EDTA•2Na•2H$_2$O [g] | Al aqueous solution (Al: 1000 ppm) [g] | Zr standard solutoin (Zr: 1000 ppm) [g] | Nb standard solutoin (Nb: 1000 ppm) [g] |
| Example C-109 | 31.0 | 38.1 | 17.5 | 13.4 | 0.02 | 0.01 | 0.005 | 0.000 | 0.000 |
| Example C-110 | 31.0 | 38.1 | 17.5 | 13.4 | 0.02 | 0.01 | 0.010 | 0.000 | 0.000 |
| Example C-111 | 31.0 | 38.1 | 17.5 | 13.4 | 0.02 | 0.01 | 0.000 | 0.010 | 0.000 |

TABLE C-9-continued

[Table 16]

| | | | | | | | | | |
|---|---|---|---|---|---|---|---|---|---|
| Example C-112 | 31.0 | 38.1 | 17.5 | 13.4 | 0.02 | 0.01 | 0.000 | 0.000 | 0.010 |
| Ref.Ex. C-102 | 31.0 | 38.1 | 17.5 | 13.4 | 0.02 | 0.01 | 0.000 | 0.000 | 0.000 |

| | | Maturation at 25° C. for 7 days after formulation | | | | | | | |
|---|---|---|---|---|---|---|---|---|---|
| No. | TPO concentration upon formulation [wt %] | Peracetic acid [wt %] | Hydrogen peroxide [wt %] | Acetic acid [wt %] | Na acetate [wt %] | Phosphorus-based HEDP [wt %] | Carboxylic acid-based EDTA•2Na [wt %] | pH | Stability |
| Example C-109 | 6.1 | 1.1 | 5.6 | 17.5 | 27.5 | 0.01 | 0.01 | 5.1 | A |
| Example C-110 | 6.1 | 1.1 | 5.6 | 17.4 | 27.5 | 0.01 | 0.01 | 5.1 | A |
| Example C-111 | 6.1 | 1.1 | 5.6 | 17.3 | 27.5 | 0.01 | 0.01 | 5.2 | B |
| Example C-112 | 6.1 | 1.1 | 5.5 | 17.3 | 27.5 | 0.01 | 0.01 | 5.2 | B |
| Ref.Ex. C-102 | 6.1 | 1.0 | 5.6 | 17.6 | 27.5 | 0.01 | 0.01 | 5.1 | A |

As described above, it was demonstrated that, according to the present invention, a composition for sterilization and cleaning of medical devices, which has high stability of peroxide and a drainage of which satisfies the sewage discharge standards, can be provided by addition of a phosphorus-based stabilizer and/or a carboxylic acid-based stabilizer as an additive(s).

The invention claimed is:

1. A composition, consisting of:
   0.001% to 15% by mass of peracetic acid;
   0.01% to 70% by mass of acetic acid and/or a salt thereof;
   0.001% to 25% by mass of hydrogen peroxide;
   water; and
   at least one additive selected from the group consisting of a phosphorus-based stabilizer and a carboxylic acid-based stabilizer, wherein
   the composition has a pH of higher than 5.0 to 10.0, and
   a concentration of the acetic acid and/or a salt thereof is greater than 10 times and 250 times or lower of a concentration of the peracetic acid.

2. The composition according to claim 1, wherein the phosphorus-based stabilizer includes at least one of 1-hydroxyethylidene-1,1-diphosphonic acid (HEDP), a salt of HEDP, diethylenetriamine penta (methylene phosphonic acid) (DTPP) or a salt of DTPP.

3. The composition according to claim 1, wherein the carboxylic acid-based stabilizer includes at least one of ethylenediaminetetraacetic acid (EDTA), a salt of EDTA, diethylenetriamine pentaacetic acid (DTPA) or a salt of DTPA.

4. The composition according to claim 1, wherein the phosphorus-based stabilizer is 1-hydroxyethylidene-1,1-diphosphonic acid (HEDP) or a salt thereof, and the carboxylic acid-based stabilizer is ethylenediaminetetraacetic acid (EDTA) or a salt thereof.

5. The composition according to claim 1, wherein the phosphorus-based stabilizer is present at 0.0001% by mass or more and less than 0.5% by mass, and the carboxylic acid-based stabilizer is present at 0.0001% by mass or more and less than 0.5% by mass.

6. The composition according to claim 1, wherein the composition has pH 5.0 to 9.0.

7. A diluted composition, consisting of:
   the composition of claim 1; and
   additional water.

8. The diluted composition according to claim 7, wherein the peracetic acid is present at 0.001% to 1.5% by mass, the acetic acid and/or a salt thereof is present at 0.01% to 7% by mass,
   the hydrogen peroxide is present at 0.001% to 2.5% by mass, and
   the diluted composition has a pH of higher than 5.0 to 10.0.

9. The composition according to claim 1 or a diluted composition thereof, wherein the hydrogen peroxide is ultrapure hydrogen peroxide.

10. The composition according to claim 1 or a diluted composition thereof, wherein the acetic acid is ultrapure acetic acid.

11. A method for producing the composition according to claim 1, comprising a mixing step of mixing at least the following components:
   (i) an additive;
   (ii) a hydrogen peroxide solution and acetic acid; and
   (iii) one or more selected from a phosphate, a citrate, and a tris base.

12. A method for producing the composition according to claim 1, comprising a mixing step of mixing at least the following components:
   (i) an additive;
   (ii) a hydrogen peroxide solution and acetic acid; and
   (iii) alkali.

13. The method for producing the composition according to claim 12, wherein the additive, acetic acid, and alkali are mixed, and then a hydrogen peroxide solution is further mixed into the mixture at 30° C. to 50° C.

14. A method for producing the composition according to claim 1, comprising a mixing step of mixing at least the following components:
   (i) an additive;
   (ii) a hydrogen peroxide solution and acetic acid; and
   (iii) acetate.

15. The method for producing the composition according to claim 11, wherein the mixing step further comprises adding a metal selected from the group consisting of Al, Zr, and Nb.

16. The composition according to claim 1, wherein the peracetic acid is present at 1.0% to 15% by mass.

17. The composition according to claim 1, wherein the pH of the composition is 6.5 to 10.0.

18. The composition according to claim 1, wherein the pH of the composition is 7.0 to 10.0.

* * * * *